US008642786B2

(12) United States Patent
Yanagihara et al.

(10) Patent No.: US 8,642,786 B2
(45) Date of Patent: Feb. 4, 2014

(54) PROCESS FOR PRODUCING THIOPHENE COMPOUND AND INTERMEDIATE THEREOF

(71) Applicant: Nissan Chemical Industries, Ltd., Chiyoda-ku (JP)

(72) Inventors: Kazufumi Yanagihara, Funabashi (JP); Shingo Umezawa, Funabashi (JP); Katsuaki Miyaji, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/833,374

(22) Filed: Mar. 15, 2013

(65) Prior Publication Data

US 2013/0204013 A1    Aug. 8, 2013
US 2014/0005413 A2    Jan. 2, 2014

Related U.S. Application Data

(62) Division of application No. 12/919,394, filed as application No. PCT/JP2009/053732 on Feb. 27, 2009, now Pat. No. 8,399,685.

(51) Int. Cl.
*C07D 333/12* (2006.01)

(52) U.S. Cl.
USPC .......................................................... 549/73

(58) Field of Classification Search
USPC .......................................................... 549/73
See application file for complete search history.

(56) References Cited

U.S. PATENT DOCUMENTS

| 8,399,685 B2 | 3/2013 | Yanagihara et al. |
| 8,420,849 B2 | 4/2013 | Yanagihara et al. |

FOREIGN PATENT DOCUMENTS

| FR | 2 447 914 | 8/1980 |
| JP | 48-26755 | 4/1973 |
| JP | 53-40755 | 4/1978 |
| JP | 54-10392 | 1/1979 |
| JP | 63-225373 | 9/1988 |
| JP | 2-300177 | 12/1990 |
| JP | 3-232880 | 10/1991 |
| JP | 5-284960 | 11/1993 |
| JP | 6-122671 | 5/1994 |
| JP | 2006-519194 | 8/2006 |
| JP | 2006-527187 | 11/2006 |
| NL | 64-13943 | 6/1965 |
| WO | WO 2007/36730 | 4/2007 |

OTHER PUBLICATIONS

Notice of Reason(s) for Refusal in corresponding Japanese Patent Application No. 2010-500780, dated Aug. 27, 2013. (w/English Translation).
I. Kumar, et al., "A Thioesterase for Chemoselective Hydrolysis of S-Acyl Sulfanylalkanoates", Organic Letters, 2001, vol. 3, No. 2, pp. 283-285.
K. Hojo, et al., "New Synthetic Reactions Based on 1-Methyl-2-Fluoropyridinium Salts. Facile Conversion of Alcohols to Thioalcohols", Chemistry Letters, 1977, pp. 133-136.
W. Yao, et al., "Study of the $Rh_2(OAc)_4$- or $BF_3$-$OEt_2$-Mediated Reaction of Thioacetic S-Acid with α-Diazocarbonyl Compounds", Eur. J. Org. Chem., 2003, pp. 1784-1788.
Y. Tanabe, et al., "Stereoselective Synthesis of Anti-Paf Active Thiazolidin-4-ones via Cyclo-condensation of Aleyl α-Mercaptocarboxylates with Arylimines", Tetrahedron letters, 1991, vol. 32, No. 3, pp. 383-386.
G. Krafft, et al., "Functionalization of Furans via Phenacyl Sulfides", Tetrahedron letters, 1991, vol. 26, No. 2, pp. 135-138.
H. Schmidt, et al., "The Clemmensen Reduction of 3-thiophane Derivatives", Thiophane Compounds., Helv. Chim. Acta, vol. 34, 1951, pp. 894-897.

*Primary Examiner* — Taofiq A Solola
(74) *Attorney, Agent, or Firm* — Oblon, Spivak, McClelland, Maier & Neustadt, L.L.P.

(57) ABSTRACT

To provide a novel process for producing a 2-aryl-3-hydroxy-4-substituted carbonyl thiophene compound or an intermediate thereof useful as an intermediate for production of medicines and agricultural chemicals.
A 2-aryl acetate compound represented by the formula (1):

wherein $R^1$ is an aryl group or the like, $R^4$ is a $C_{1-3}$ alkyl group or the like, and X is a leaving group, is reacted with a thioacetic acid compound to form a thioacetyl compound (3), the thioacetyl compound (3) is reacted with a vinyl ketone compound to form a γ-ketosulfide compound (5), which is cyclized under basic conditions to form a dihydrothiophene compound (6), and the dihydrothiophene compound (6) is oxidized by using an oxidizing agent to produce a 2-aryl-3-hydroxy-4-substituted carbonyl thiophene compound (7).

4 Claims, No Drawings

PROCESS FOR PRODUCING THIOPHENE COMPOUND AND INTERMEDIATE THEREOF

This application is a Divisional of U.S. application Ser. No. 12/919,394, filed on Aug. 25, 2010, now allowed, which is a National Stage of PCT/JP2009/053732, filed on Feb. 27, 2009.

TECHNICAL FIELD

The present invention relates to a process for producing, from a 2-aryl acetate compound, a corresponding 2-aryl-3-hydroxy-4-substituted carbonyl thiophene compound or an intermediate thereof.

BACKGROUND ART

2-Aryl-3-hydroxy-4-substituted carbonyl thiophene compounds are compounds useful, for example, as intermediates for synthesis of thrombopoietin receptor activators (e.g. Patent Document 1).

As a process for producing a 2-aryl-3-hydroxy-4-substituted carbonyl thiophene compound, only a process of synthesizing a 2-aryl-3-hydroxy-4-ester thiophene compound by a known production process (e.g. Patent Document 2), and converting the ester group at the 4-position to an alkylcarbonyl group has been known (e.g. Patent Document 1). However, conversion of the ester group to an alkylcarbonyl group requires multiple steps, and thus a production process with a smaller number of steps has been desired.

As a production process which seems to be applicable to production of a 2-aryl-3-hydroxy-4-substituted carbonyl thiophene compound, a process for producing a 2-methylcarbonyl-3-hydroxy-4-substituted carbonyl thiophene compound, the 2-position of which is substituted with methylcarbonyl not with aryl (Non-Patent Document 1), a process for producing a 3-hydroxy-4-methylcarbonyl thiophene compound, the 2-position of which is unsubstituted, not substituted with aryl, or the like may be conceivable. However, these Non-Patent Documents failed to disclose a process for producing a 2-aryl-3-hydroxy-4-substituted carbonyl thiophene compound.

Patent Document 1: WO2004/108683
Patent Document 2: JP-A-48-26755
Non-Patent Document 1: J. CHEM. RESEARCH(S), 12, 386, 1985
Non-Patent Document 2: J. CHEM. RESEARCH (M), 4135, 1985

DISCLOSURE OF THE INVENTION

Object to be Accomplished by the Invention

The object of the present invention is to provide a novel process for producing a 2-aryl-3-hydroxy-4-substituted carbonyl thiophene compound or an intermediate thereof, useful as an intermediate for production of medicines and agricultural chemicals.

Means to Accomplish the Object

The present inventors have conducted extensive studies to accomplish the above object and as a result, found the following novel process for producing a 2-aryl-3-hydroxy-4-substituted carbonyl thiophene compound or an intermediate thereof, and accomplished the present invention.

That is, the present invention provides the following.
(I) A process for producing a thiophene compound or an intermediate thereof, which comprises reacting a 2-aryl acetate compound represented by the formula (1):

(1)

wherein $R^1$ means a $C_{6-10}$ aryl group, a $C_{1-5}$ heteroaryl group (the $C_{6-10}$ aryl group and the $C_{1-5}$ heteroaryl group are unsubstituted or substituted with a halogen atom, a carboxy group, a nitro group, a formyl group, a cyano group, a hydroxy group, a protected hydroxy group, a thiol group, an amino group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group or a $C_{6-10}$ aryl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group and the $C_{6-10}$ aryl group are unsubstituted or substituted with a halogen atom)), $R^4$ means a $C_{1-3}$ alkyl group (the $C_{1-3}$ alkyl group is unsubstituted or substituted with a halogen atom), and X means a leaving group, with a thioacetic acid compound represented by the formula (2):

$$AcSM \qquad (2)$$

wherein Ac means an acetyl group (the acetyl group is unsubstituted or substituted with a $C_{1-3}$ alkyl group (the $C_{1-3}$ alkyl group is unsubstituted or substituted with a halogen atom) or a halogen atom), and M means a hydrogen atom or a metal salt, to form a thioacetyl compound represented by the formula (3):

(3)

hydrolyzing the thioacetyl compound, reacting the resulting thiol compound after isolated or without being isolated with a vinyl ketone compound represented by the formula (4):

(4)

wherein each of $R^2$ and $R^3$ which are independent of each other, means a hydrogen atom, a $C_{1-6}$ alkyl group or a $C_{6-10}$ aryl group (the $C_{1-6}$ alkyl group and the $C_{6-10}$ aryl group are unsubstituted or substituted with a halogen atom, a nitro group, a cyano group, a hydroxy group, a protected hydroxy group, a thiol group, an amino group, a $C_{1-10}$ alkyl group, a $C_{2-6}$ alkenyl group, a $C_{2-6}$ alkynyl group, a $C_{1-10}$ alkoxy group or a $C_{6-10}$ aryl group (the $C_{1-10}$ alkyl group, the $C_{2-6}$ alkenyl group, the $C_{2-6}$ alkynyl group, the $C_{1-10}$ alkoxy group and the $C_{6-10}$ aryl group are unsubstituted or substituted with a halogen atom)), to form a γ-ketosulfide compound represented by the formula (5):

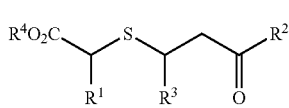
(5)

cyclizing the γ-ketosulfide compound under basic conditions to form a dihydrothiophene compound represented by the formula (6):

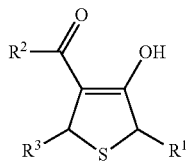
(6)

and oxidizing it by using an oxidizing agent to produce a 2-aryl-3-hydroxy-4-substituted carbonyl thiophene compound represented by the formula (7):

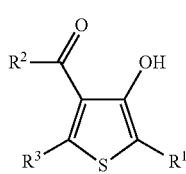
(7)

(II) A process for producing a thiophene compound or an intermediate thereof, which comprises hydrolyzing a thio-acetyl compound (3):

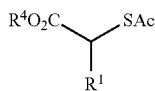
(3)

wherein $R^1$ and $R^4$ are as defined in (I), and reacting the resulting thiol compound after isolated or without being isolated with a vinyl ketone compound represented by the formula (4):

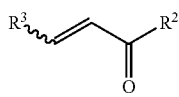
(4)

wherein $R^2$ and $R^3$ are as defined in (I), to form a γ-ketosulfide compound represented by the formula (5):

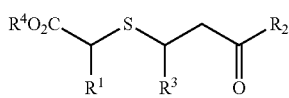
(5)

and cyclizing the γ-ketosulfide compound under basic conditions to produce a 2-aryl-3-hydroxy-4-substituted carbonyl dihydrothiophene compound represented by the formula (6):

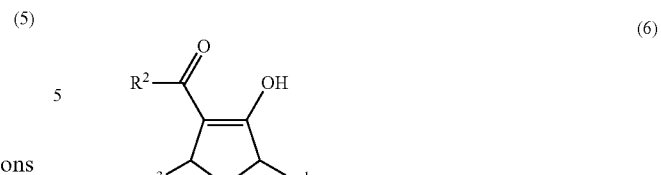
(6)

(III) A process for producing a thiophene compound or an intermediate thereof, which comprises hydrolyzing a thio-acetyl compound (3):

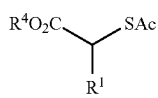
(3)

wherein $R^1$ and $R^4$ are as defined in (I), and reacting the resulting thiol compound after isolated or without being isolated with a vinyl ketone compound represented by the formula (4):

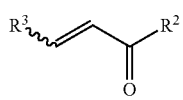
(4)

wherein $R^2$ and $R^3$ are as defined in (I), to produce a γ-ketosulfide compound represented by the formula (5):

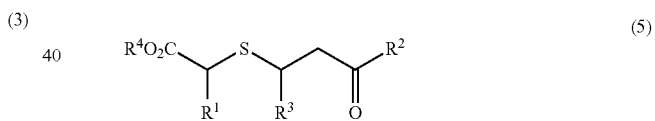
(5)

(IV) A process for producing a thiophene compound or an intermediate thereof, which comprises hydrolyzing a thio-acetyl compound (3):

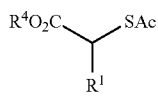
(3)

wherein $R^1$ and $R^4$ are as defined in (I), under acidic conditions, and reacting the resulting thiol compound without being isolated with a vinyl ketone compound represented by the formula (4):

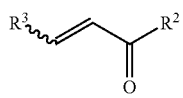
(4)

wherein $R^2$ and $R^3$ are as defined in (I), to produce a γ-ketosulfide compound represented by the formula (5):

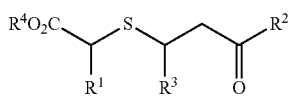
(5)

(V) A process for producing a thiophene compound or an intermediate thereof, which comprises cyclizing a γ-ketosulfide compound represented by the formula (5):

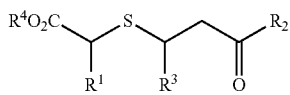
(5)

wherein $R^1$, $R^2$, $R^3$ and $R^4$ are as defined in (I), under basic conditions to produce a 2-aryl-3-hydroxy-4-substituted carbonyl dihydrothiophene compound represented by the formula (6):

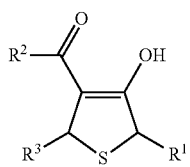
(6)

(VI) The process for producing a thiophene compound or an intermediate thereof according to any one of the above (I) to (V), wherein $R^1$ is a $C_{6-10}$ aryl group (the $C_{6-10}$ aryl group is unsubstituted or substituted with a halogen atom, a $C_{1-10}$ alkyl group or a $C_{1-10}$ alkoxy group (the $C_{1-10}$ alkyl group and the $C_{1-10}$ alkoxy group are unsubstituted or substituted with a halogen atom)).
(VII) The process for producing a thiophene compound or an intermediate thereof according to any one of the above (I) to (VI), wherein $R^2$ is a $C_{1-3}$ alkyl group (the $C_{1-3}$ alkyl group is unsubstituted or substituted with a halogen atom).
(VIII) The process for producing a thiophene compound or an intermediate thereof according to any one of the above (I) to (VII), wherein $R^3$ is a hydrogen atom or a methyl group.
(IX) The process for producing a thiophene compound or an intermediate thereof according to any one of the above (I) to (VIII), wherein $R^4$ is a methyl group.
(X) The process for producing a thiophene compound or an intermediate thereof according to any one of the above (I) to (IX), wherein $R^1$ is a phenyl group (the phenyl group is unsubstituted or substituted with a halogen atom, a $C_{1-10}$ alkyl group or a $C_{1-10}$ alkoxy group (the $C_{1-10}$ alkyl group and the $C_{1-10}$ alkoxy group are unsubstituted or substituted with a halogen atom)).

BEST MODE FOR CARRYING OUT THE INVENTION

Now, the present invention will be described in detail. In the present invention, "n" denotes normal, "i" denotes iso, "s" or "sec" denotes secondary, "t" or "tert" denotes tertiary, "c" denotes cyclo, "o" denotes ortho, "m" denotes meta, "p" denotes para, "Me" denotes a methyl group, "Bu" denotes a butyl group, and "tBu" denotes a tertiary butyl group.

The $C_{1-10}$ alkyl group in the present invention means a linear, branched or cyclic alkyl group containing 1 to 10 carbon atoms and may, for example, be a methyl group, an ethyl group, a n-propyl group, a n-butyl group, a n-pentyl group, a n-hexyl group, a n-heptyl group, a n-octyl group, a n-decyl group, an i-propyl group, an i-butyl group, a t-butyl group, a s-butyl group, an i-pentyl group, a neopentyl group, a t-pentyl group, a c-propyl group or a c-butyl group, and is more preferably a methyl group, an ethyl group or an i-propyl group.

The $C_{1-3}$ alkyl group in the present invention means a linear, branched or cyclic alkyl group containing 1 to 3 carbon atoms, and may, for example, be a methyl group, an ethyl group, a n-propyl group, an i-propyl group or a c-propyl group, and is more preferably a methyl group, an ethyl group or an i-propyl group.

The $C_{2-6}$ alkenyl group in the present invention means a linear, branched or cyclic alkenyl group containing 2 to 6 carbon atoms, and may, for example, be ethenyl, 1-propenyl, 2-propenyl, 1-methyl-1-ethenyl, 1-butenyl, 2-pentenyl, 3-hexenyl, 4-methyl-2-pentenyl or 3-c-pentenyl, and is more preferably ethenyl, 1-propenyl or 2-propenyl.

The $C_{2-6}$ alkynyl group in the present invention means a linear, branched or cyclic alkenyl group containing 2 to 6 carbon atoms, and may, for example, be ethynyl, 1-propynyl, 2-propynyl, 1-methyl-1-ethynyl, 1-butynyl, 2-pentynyl, 3-hexynyl, 4-methyl-2-pentynyl or 3-c-pentynyl, and is more preferably ethynyl, 1-propynyl or 2-propynyl.

The $C_{1-10}$ alkoxy group in the present invention means a linear or branched alkoxy group containing 1 to 10 carbon atoms, and may, for example, be a methoxy group, an ethoxy group, a n-propoxy group, an i-propoxy group, a n-butoxy group, an i-butoxy group, a s-butoxy group, a t-butoxy group, a n-pentyloxy group, an i-pentyloxy group or n-hexyloxy group, and is more preferably a methoxy group or an ethoxy group.

The $C_{1-10}$ alkylcarbonyl group in the present invention means a carbonyl group substituted with a $C_{1-10}$ alkyl group, and may, for example, be a methylcarbonyl group, an ethylcarbonyl group, a n-propylcarbonyl group, a n-butylcarbonyl group, a n-pentylcarbonyl group, a n-hexylcarbonyl group, a n-octylcarbonyl group, a n-decylcarbonyl group, an i-propylcarbonyl group, an i-butylcarbonyl group, a t-butylcarbonyl group, a s-butylcarbonyl group, an i-pentylcarbonyl group, a neopentylcarbonyl group, a t-pentylcarbonyl group, a c-propylcarbonyl group or a c-butylcarbonyl group, and is more preferably a methylcarbonyl group, an ethylcarbonyl group or an i-propylcarbonyl group.

The $C_{1-10}$ alkylcarbonyloxy group in the present invention means a carbonyloxy group substituted with a $C_{1-10}$ alkyl group, and may, for example, be a methylcarbonyloxy group, an ethylcarbonyloxy group, a n-propylcarbonyloxy group, a n-butylcarbonyloxy group, a n-pentylcarbonyloxy group, a n-hexylcarbonyloxy group, a n-octylcarbonyloxy group, a n-decylcarbonyloxy group, an i-propylcarbonyloxy group, an i-butylcarbonyloxy group, a t-butylcarbonyloxy group, a s-butylcarbonyloxy group, an i-pentylcarbonyloxy group, a neopentylcarbonyloxy group, a t-pentylcarbonyloxy group, a c-propylcarbonyloxy group or a c-butylcarbonyloxy group, and is more preferably a methylcarbonyloxy group, an ethylcarbonyloxy group or an i-propylcarbonyloxy group.

The $C_{1-10}$ alkoxycarbonyl group in the present invention means a carbonyl group substituted with a $C_{1-10}$ alkoxy group, and may, for example, be a methoxycarbonyl group, an ethoxycarbonyl group, a n-propoxycarbonyl group, an i-propoxycarbonyl group, a n-butoxycarbonyl group, an i-butoxycarbonyl group, a s-butoxycarbonyl group, a t-butoxycarbonyl group, a n-pentyloxycarbonyl group, an i-pentyloxycarbonyl group or a n-hexyloxycarbonyl group, and is more preferably a methoxycarbonyl group or an ethoxycarbonyl group.

The $C_{6-10}$ aryl group in the present invention means an aromatic hydrocarbon containing 6 to 10 carbon atoms, and as its specific examples, a phenyl group, an α-naphthyl group and a β-naphthyl group may be mentioned.

The $C_{1-5}$ heteroaryl group in the present invention means a 5 to 7 membered aromatic heteromonocyclic ring containing 1 to 5 carbon atoms and containing 1 to 3 oxygen atoms, nitrogen atoms or sulfur atoms singly or in combination, and as its specific examples, a pyridyl group, a pyramidinyl group, a pyrrolyl group, a furyl group, a thienyl group, a thiazolyl group, a tetrazole group and a triazole group may be mentioned.

A halogen atom is a fluorine atom, a chlorine atom, a bromine atom, an iodine atom or the like.

Now, $R^1$, $R^2$, $R^3$, $R^4$, X, Ac and M in the compounds of the present invention will be described.

$R^1$ is preferably a $C_{6-10}$ aryl group (the $C_{6-10}$ aryl group is unsubstituted or substituted with a halogen atom, a $C_{1-10}$ alkyl group or a $C_{1-10}$ alkoxy group (the $C_{1-10}$ alkyl group and the $C_{1-10}$ alkoxy group are unsubstituted or substituted with a halogen atom)). $R^1$ is more preferably a phenyl group (the phenyl group is unsubstituted or substituted with a halogen atom, a $C_{1-10}$ alkyl group or a $C_{1-10}$ alkoxy group (the $C_{1-10}$ alkyl group and the $C_{1-10}$ alkoxy group are unsubstituted or substituted with a halogen atom)), furthermore preferably a 3,4-dichlorophenyl group, a 4-chlorophenyl group, a 4-bromophenyl group, a 4-trifluoromethylphenyl group, a 4-trifluoromethoxyphenyl group, a 3,4-dimethylphenyl group or a 4-t-butylphenyl group.

$R^2$ is preferably a hydrogen atom or a $C_{1-3}$ alkyl group (the $C_{1-3}$ alkyl group may optionally be substituted with a halogen atom). $R^2$ is more preferably a $C_{1-3}$ alkyl group, particularly preferably a methyl group.

$R^3$ is preferably a hydrogen atom or a methyl group, more preferably a hydrogen atom.

$R^4$ is preferably a $C_{1-3}$ alkyl group. $R^4$ is more preferably a methyl group or an ethyl group, particularly preferably a methyl group.

As the leaving group X, a halogen atom such as a chlorine atom, a bromine atom or an iodine atom, a methanesulfonyloxy group, a trifluoromethanesulfonyloxy group or a p-toluenesulfonyloxy group may, for example, be used. The leaving group is more preferably a halogen atom, furthermore preferably a bromine atom.

The Ac group is not particularly limited so long as thioacetylation and the subsequent hydrolysis of a thioacetyl group are possible, but is preferably an unsubstituted or substituted acetyl group. More preferred is an acetyl group (the acetyl group is unsubstituted or substituted with a $C_{1-3}$ alkyl group (the $C_{1-3}$ alkyl group is unsubstituted or substituted with a halogen atom) or a halogen atom), furthermore preferred is a trifluoromethylcarbonyl group or a methylcarbonyl group, and particularly preferred is a methylcarbonyl group.

In the production process of the present invention, any reaction solvent that is stable under the reaction conditions and inert enough not to hinder the reaction may be used without any particular restrictions. Such a solvent may, for example, be water, an alcohol (such as methanol, ethanol, propanol, butanol or octanol), a cellosolve (such as methoxyethanol or ethoxyethanol), an aprotic polar organic solvent (such as dimethylformamide, dimethylsulfoxide, dimethylacetamide, tetramethylurea, sulfolane, N-methylpyrrolidone or N,N-dimethylimidazolidinone), an ether (such as diethyl ether, diisopropyl ether, t-butyl methyl ether, tetrahydrofuran or dioxane), an aliphatic hydrocarbon (such as pentane, hexane, c-hexane, heptane, octane, decane, decalin or petroleum ether), an aromatic hydrocarbon (such as benzene, chlorobenzene, o-dichlorobenzene, nitrobenzene, toluene, xylene, mesitylene or tetralin), a halogenated hydrocarbon (such as chloroform, dichloromethane, dichloroethane or carbon tetrachloride), a ketone (such as acetone, methyl ethyl ketone, methyl butyl ketone or methyl isobutyl ketone), a lower aliphatic acid ester (such as methyl acetate, ethyl acetate, butyl acetate or methyl propionate), an alkoxyalkane (such as dimethoxyethane or diethoxyethane) or a nitrile (such as acetonitrile, propionitrile or butyronitrile). One or more are suitably selected from these solvents in accordance with reactivity and used alone or as a mixture. Further, in some cases, the solvent is used as a nonaqueous solvent using a proper dehydrating agent or drying agent. The above-described solvents are examples to carry out the present invention, and the present invention is not limited to these conditions.

As examples of the thioacetic acid compound (2) used to thioacetylate the 2-aryl acetate compound (1), thioacetic acid, potassium thioacetate and sodium thioacetate may be mentioned, and potassium thioacetate is particularly preferred.

Further, as a solvent for the thioacetylation reaction, the above-described reaction solvent may be used. The reaction solvent is more preferably an alcohol, furthermore preferably methanol.

The amount of use of the thioacetic acid compound is from 1 to 10 molar equivalents based on the amount of use of the 2-aryl acetate compound (1), and is preferably from 1 to 2 molar equivalents, more preferably from 1.1 to 1.6 molar equivalents in view of handling efficiency and economical efficiency.

The reaction temperature of the thioacetylation reaction is preferably from −20° C. to 60° C., more preferably from 0° C. to 40° C. In a case where $R^1$ is a $C_{6-10}$ aryl group substituted with an electron-withdrawing group, the reaction temperature of the thioacetylation is furthermore preferably from 0° C. to 29° C., particularly preferably from 00° C. to 10° C. In a case where $R^1$ is a $C_{6-10}$ aryl group substituted with an electron-donating group, the reaction temperature of the thioacetylation is furthermore preferably from 30° C. to 40° C.

The hydrolysis reaction of the thioacetyl compound (3) of the present invention may be carried out in the absence of an acid or a base, but the hydrolysis is carried out preferably in the presence of an acid or a base in view of handling efficiency, etc. Particularly, the hydrolysis is carried out in the presence of an acid.

The acid to be used for the hydrolysis reaction of the thioacetyl compound (3), may, for example, be an inorganic acid such as hydrochloric acid, hydrobromic acid, hydroiodic acid, sulfuric acid, nitric acid, phosphoric acid or polyphosphoric acid, or an organic acid such as p-toluenesulfonic acid, methanesulfonic acid, trifluoroacetic acid, formic acid or acetic acid. The acid is more preferably an inorganic acid, furthermore preferably hydrochloric acid or sulfuric acid, particularly preferably hydrochloric acid.

The amount of use of the acid is from 0.1 to 10 molar equivalents based on the amount of use of the thioacetyl compound (3), and is preferably from 0.1 to 2 molar equivalents, more preferably from 0.25 to 1.5 molar equivalents in view of handling efficiency and economical efficiency.

The reaction temperature of the hydrolysis reaction of the thioacetyl compound (3) with an acid is preferably from 25°

C. to the reflux temperature of the solvent, more preferably from 55 to 70° C., furthermore preferably from 60 to 65° C.

As the solvent to be used for the hydrolysis reaction of the thioacetyl compound (3) with an acid, the above-described reaction solvent may be used. The reaction solvent is more preferably an alcohol, furthermore preferably methanol.

The base to be used for the hydrolysis reaction of the thioacetyl compound (3) may, for example, be a hydroxide of an alkali metal such as lithium hydroxide, sodium hydroxide, potassium hydroxide, magnesium hydroxide, calcium hydroxide or barium hydroxide. Particularly preferred is sodium hydroxide.

The amount of use of the base is from 1 to 5 molar equivalents based on the amount of use of the thioacetyl compound (3), and is preferably from 1 to 2 molar equivalents in view of handling efficiency and economical efficiency.

As the solvent to be used for the hydrolysis reaction of the thioacetyl compound (3) with a base, the above-described reaction solvent may be used. The reaction solvent is more preferably an alcohol, furthermore preferably methanol.

The thiol compound obtained by hydrolyzing the thioacetyl compound (3) may be reacted with the vinyl ketone compound (4) after isolated or without being isolated, but is preferably reacted with the vinyl ketone compound (4) without being isolated in order to avoid bad smell of the thiol compound and a side-reaction during the post-processing.

The base to be used for the reaction of the thiol compound formed by the hydrolysis reaction of the thioacetyl compound (3) with the vinyl ketone compound (4) may, for example, be an amine such as diethylamine, triethylamine, diisopropylethylamine, tri-n-propylamine, tri-n-butylamine, DBN (diazabicyclononane), DBU (diazabicycloundecene), N-methylmorpholine or N,N-dimethylaniline; a pyridine such as pyridine, methyl ethyl pyridine, lutidine or 4-N,N-dimthylaminopyridine; an imidazole; a pyrazole; a hydroxide of an alkali metal or an alkaline earth metal such as lithium hydroxide, sodium hydroxide, potassium hydroxide, magnesium hydroxide, calcium hydroxide or barium hydroxide; a carbonate of an alkali metal or an alkaline earth metal such as sodium carbonate, potassium carbonate, cesium carbonate, magnesium carbonate, calcium carbonate or barium carbonate; a metal alkoxide such as sodium methoxide, sodium ethoxide or potassium t-butoxide; an alkali metal amide such as sodium amide or lithium amide; or an alkali metal hydride such as sodium hydride or lithium hydride. The base is more preferably an amine, furthermore preferably triethylamine or diisopropylethylamine, particularly preferably triethylamine.

The amount of use of the base is from 0.5 to 10 molar equivalents based on the amount of use of the thiol compound, and is preferably from 0.5 to 3 molar equivalents, more preferably from 0.75 to 2 molar equivalents in view of handling efficiency and economical efficiency. Further, in a case where an acid is used for the hydrolysis reaction of the thioacetyl compound (3), it is preferred to add the base in excess to the equivalent amount of the acid used.

The amount of use of the vinyl ketone compound (4) to be used for the reaction with the thiol compound obtained by hydrolyzing the thioacetyl compound (3) is from 1 to 10 molar equivalents based on the amount of use of the thiol compound, and is preferably from 1 to 2 molar equivalents, more preferably from 1.0 to 1.5 molar equivalents in view of handling efficiency and economical efficiency.

The temperature of the reaction of the thiol compound obtained by hydrolyzing the thioacetyl compound (3) with the vinyl ketone compound (4) is preferably from 0 to 60° C., more preferably from 10 to 20° C.

As the solvent of the reaction of the thiol compound obtained by hydrolyzing the thioacetyl compound (3) with the vinyl ketone compound (4), the above-described reaction solvent may be used. The reaction solvent is preferably an aprotic polar organic solvent, more preferably ethyl acetate or toluene. In a case where the thiol compound is reacted with the vinyl ketone compound (4) without being isolated, the reaction solvent is a mixed solvent with the reaction solvent in the hydrolysis step.

Now, cyclization of the γ-ketosulfide compound (5) obtained by reaction of the thiol compound obtained by hydrolyzing the thioacetyl compound (3) with the vinyl ketone compound (4) will be described.

In the cyclization of the γ-ketosulfide compound (5), the base may, for example, be an amine such as diethylamine, triethylamine, diisopropylethylamine, tri-n-propylamine, tri-n-butylamine, DBN (diazabicyclononane), DBU (diazabicycloundecene), N-methylmorpholine or N,N-dimethylaniline; a pyridine such as pyridine, methyl ethyl pyridine, lutidine or 4-N,N-dimthylaminopyridine; an imidazole; a pyrazole; a hydroxide of an alkali metal or an alkaline earth metal such as lithium hydroxide, sodium hydroxide, potassium hydroxide, magnesium hydroxide, calcium hydroxide or barium hydroxide; a carbonate of an alkali metal or an alkaline earth metal such as sodium carbonate, potassium carbonate, cesium carbonate, magnesium carbonate, calcium carbonate or barium carbonate; a metal alkoxide such as sodium methoxide, sodium ethoxide or potassium t-butoxide; an alkali metal amide such as sodium amide or lithium amide; or an alkali metal hydride such as sodium hydride or lithium hydride. The base is preferably a metal alkoxide such as sodium methoxide, sodium ethoxide or potassium t-butoxide; an alkali metal amide such as sodium amide or lithium amide; or an alkali metal hydride such as sodium hydride or lithium hydride, more preferably an alkali metal amide such as sodium amide or lithium amide or a metal alkoxide such as sodium methoxide, sodium ethoxide or potassium t-butoxide, particularly preferably sodium amide or sodium methoxide.

The amount of use of the base is from 1 to 10 molar equivalents base on the amount of use of the γ-ketosulfide compound (5), and is preferably from 1 to 2 molar equivalents, more preferably from 1.5 to 2.0 molar equivalents in view of handling efficiency and economical efficiency.

In the cyclization of the γ-ketosulfide compound (5), as the solvent, the above-described reaction solvent may be used. The reaction solvent is more preferably an alcohol, furthermore preferably ethanol or isopropanol. In a case where the solvent is not distilled off after the post processing in the previous step, the reaction may be carried out in a mixed solvent with the solvent in the previous step.

In the formation of a thiophene from the dihydrothiophene compound (6), as the oxidizing agent, hydrogen peroxide, sulfuryl chloride, sodium hypochlorite or Oxone (manufactured by DuPont, trademark) may, for example, be used. The oxidizing agent is preferably hydrogen peroxide or sulfuryl chloride.

The amount of use of the oxidizing agent is from 1 to 10 molar equivalents based on the amount of use of the dihydrothiophene compound (6), and is preferably from 0.9 to 3.0 molar equivalents. In a case where sulfuryl chloride is used as the oxidizing agent, the amount of use is preferably from 0.9 to 1.1 molar equivalents with a view to suppressing by-products. In a case where hydrogen peroxide is used as the oxidizing agent, the amount of use is preferably from 2 to 4 molar equivalents, more preferably from 2 to 2.5 molar equivalents.

As the solvent in the formation of a thiophene, the above-described reaction solvent may be used. The reaction solvent is more preferably a halogenated hydrocarbon or an alcohol. In a case where sulfuryl chloride is used as the oxidizing agent, the reaction solvent is more preferably chloroform or dichloromethane, particularly preferably chloroform. In a case where hydrogen peroxide is used as the oxidizing agent, the reaction solvent is more preferably an alcohol, particularly preferably methanol.

In a case where the compounds used or intermediates or products formed in the production process of the present invention include isomers such as tautomers, geometric isomers and optical isomers, the production process of the present invention includes production processes using or producing such isomers or a mixture of isomers.

EXAMPLES

Now, the present invention will be described in further detail with reference to Examples, but it should be understood that the present invention is by no means restricted to such specific Examples.

The $^1$H-NMR analysis was carried out at 300 MHz, and LC/MS was measured under the following conditions.

Further, NMR denotes nuclear magnetic resonance, LC/MS liquid chromatography mass spectrometry, and ESI electrospray ionization.

LC/MS Condition 1
  Column: SunFire C18 manufactured by Waters (average particle size of filler: 3.5 μm, column inner diameter×column length=4.6 mm×30 mm, the same applies hereinafter)
  Eluent: Acetonitrile/0.1 vol % aqueous formic acid solution (10/90→60/40 (vol %), the same applies hereinafter)

LC/MS Condition 2
  Column: SunFire C18 manufactured by Waters (3.5 μm, 4.6 mm×30 mm)
  Eluent: Acetonitrile/0.1 vol % aqueous formic acid solution (10/90→85/15)

LC/MS Condition 3
  Column: SunFire C18 manufactured by Waters (3.5 μm, 4.6 mm×30 mm)
  Eluent: Acetonitrile/0.1 vol % aqueous formic acid solution (20/80→100/0)

LC/MS Condition 4
  Column: XTerra MSC18 manufactured by Waters (5 μm, 4.6 mm×50 mm)
  Eluent: Acetonitrile/0.1 vol % aqueous formic acid solution (10/90→60/40)

LC/MS Condition 5
  Column: XTerra MSC18 manufactured by Waters (3.5 μm, 2.1 mm×20 mm)
  Eluent: Acetonitrile/0.2 vol % aqueous formic acid solution (20/80→90/10)

LC/MS Condition 6
  Column: XTerra MSC18 manufactured by Waters (3.5 μm, 2.1 mm×20 mm)
  Eluent: Acetonitrile/0.2 vol % aqueous formic acid solution (20/80-90/10)

Reference Synthetic Example 1

Methyl 2-(3,4-dichlorophenyl)acetate

Methanol (59 mL, 3.0 equivalent amounts) was added to a 1,2-dichloroethane (400 mL) solution of 2-(3,4-dichlorophenyl) acetic acid (100 g, 0.488 mol). The solution was heated to 50° C., and then concentrated sulfuric acid (10 mL) was dropwise added over a period of 15 minutes, followed by stirring at 50° C. for 1.5 hours. The reaction solution was cooled to room temperature, followed by liquid separation to remove a sulfuric acid layer, and the obtained organic layer was sequentially washed with water, a saturated sodium hydrogencarbonate aqueous solution and a saturated salt solution, and dried over anhydrous magnesium sulfate. The drying agent was removed by filtration, and the solvent was distilled off to give the desired product as a colorless oil (105 g, yield: 98%).

$^1$H-NMR (300 MHz, ppm in CDCl$_3$)
δ:3.59 (s, 2H), 3.71 (s, 3H), 7.12 (dd, J=8.4 Hz, 1.8 Hz, 1H), 7.38-7.41 (m, 2H).

Reference Synthetic Examples 2, 3, 4 and 6

Compounds were synthesized in accordance with Reference Synthetic Example 1. The NMR analysis data of the compounds are shown below.

Reference Synthetic Example 2

$^1$H-NMR (300 MHz, ppm in CDCl$_3$)
δ:1.32 (s, 9H), 3.60 (s, 2H), 3.70 (s, 3H), 7.19-7.22 (m, 2H), 7.33-7.36 (m, 2H).

Reference Synthetic Example 3

$^1$H-NMR (300 MHz, ppm in CDCl$_3$)
δ:3.58 (s, 2H), 3.70 (s, 3H), 7.16 (dd, J=8.4 Hz, 2.1 Hz, 2H), 7.45 (J=8.4 Hz, 2.1 Hz, 2H).

Reference Synthetic Example 4

$^1$H-NMR (300 MHz, ppm in CDCl$_3$)
δ:3.58 (s, 2H), 3.70 (s, 3H), 7.20-7.31 (m, 4H).

Reference Synthetic Example 6

$^1$H-NMR (300 MHz, ppm in CDCl$_3$)
δ:3.58 (s, 2H), 3.71 (s, 3H), 7.40 (d, J=8.6 Hz, 2H), 7.59 (d, J=8.6 Hz, 2H).

Reference Synthetic Examples 5, 7, 8, 10 and 12

Compounds were synthesized in accordance with Reference Synthetic Example 1. The morphology and the LC/MS analysis data of the compounds are shown below.

TABLE 1

| Reference Synthetic Examples | Morphology | LC/MS condition | Observed peak (ESI+) | Observed peak (ESI−) | Retention time (min) |
|---|---|---|---|---|---|
| 5 | Colorless oil | 2 | 185.01 | — | 3.02 |
| 7 | Pale yellow oil | 1 | 118.96 (M + 1 − CO$_2$Me) | — | 3.77 |
| 8 | Colorless oil | 3 | 235 | — | 2.77 |
| 10 | Colorless oil | 3 | 221, 223 | — | 2.82 |
| 12 | Colorless oil | 2 | 108.97 (M + 1 − CO$_2$Me) | — | 2.77 |

Reference Synthetic Example 13

Methyl 2-(3,4-dichlorophenyl)-2-bromoacetate

N-bromosuccinimide (116 g, 1.4 equivalent amounts) was added to a 1,2-dichloroethane (320 mL) solution of methyl 2-(3,4-dichlorophenyl)acetate (106.8 g, 0.446 mol) at room temperature, followed by heating to 85° C. To this solution, a 1,2-dichloroethane (22.6 mL) solution of benzoyl peroxide (2.26 g, 2.0 mol %) was dropwise added dividedly 10 times every 10 minutes, followed by stirring at 85° C. for 3 hours. The reaction solution was cooled to room temperature, sequentially washed with a 2M sodium hydroxide aqueous solution, a mixed liquid of water-sodium thiosulfate aqueous solution (2:1, (v/v)), a saturated ammonium chloride aqueous solution and a saturated salt solution, and dried over anhydrous magnesium sulfate. The drying agent was removed by filtration, and the solvent was distilled off to give the desired product as a brown oil (142 g, yield: 103%).

$^1$H-NMR (300 MHz, ppm in CDCl$_3$)
δ:3.81 (s, 3H), 5.27 (s, 1H), 7.37-7.47 (m, 2H), 7.66 (d, J=2.1 Hz, 1H).

Reference Synthetic Example 19

Methyl 2-(3,4-dimethylphenyl)-2-bromoacetate

In a nitrogen gas atmosphere, a 1.56 M n-butyllithium/n-hexane solution (56.77 mL, 88.57 mmol) was dropwise added to a dehydrated tetrahydrofuran (150 mL) solution of 1,1,1,3,3,3-hexamethyldisilazane (15.60 g, 92.78 mmol) at about –30° C. over a period of 10 minutes, followed by stirring at about –40° C. for 30 minutes. Then, to the reaction solution, a dehydrated tetrahydrofuran (150 mL) solution of methyl 2-(3,4-dimethylphenyl) acetate (15.03 g, 84.35 mmol) was dropwise added over a period of 20 minutes. This reaction solution was dropwise added to a dehydrated tetrahydrofuran (150 mL) solution of bromine (4.54 mmol, 88.57 mmol) in a nitrogen gas atmosphere at about –35° C. over a period of 1 hour. After stirring at about –35° C. for 1 hour, the temperature was raised to 0° C., and a mixed liquid of water-sodium thiosulfate aqueous solution (1:1, (v/v)) was added to the reaction solution, and extracted with ethyl acetate. Then, the extract was washed with a saturated ammonium chloride aqueous solution and a saturated salt solution and dried over anhydrous magnesium sulfate. The drying agent was removed by filtration, and the solvent was distilled off to give the desired product as a red oil (18.23 g, yield: 84%).

LC/MS: Condition 1, retention time 4.10 (min)
LC/MS (ESI$^+$) m/z; 177.05 [M+1−Br]
$^1$H-NMR (ppm in CDCl$_3$, 300 MHz) δ: 2.25 (s, 3H), 2.27 (s, 3H), 3.78 (s, 3H), 5.33 (s, 1H), 7.12 (d, J=8.1 Hz, 1H), 7.25-7.28 (multi, 1H), 7.31 (br.s, 1H).

Reference Synthetic Examples 14, 15, 16 and 18

Compounds were synthesized in accordance with Reference Synthetic Example 13.
The NMR analysis data of the compounds are shown below.

Reference Synthetic Example 14

$^1$H-NMR (300 MHz, ppm in CDCl$_3$)
δ:1.32 (s, 9H), 3.79 (s, 3H), 5.36 (s, 1H), 7.37-7.40 (m, 2H), 7.45-7.49 (m, 1H).

Reference Synthetic Example 15

$^1$H-NMR (300 MHz, ppm in CDCl$_3$)
δ:3.79 (s, 3H), 5.30 (s, 1H), 7.40-7.57 (m, 4H).

Reference Synthetic Example 16

$^1$H-NMR (300 MHz, ppm in CDCl$_3$)
δ:3.80 (s, 3H), 5.32 (s, 1H), 7.29-7.64 (m, 4H).

Reference Synthetic Example 18

$^1$H-NMR (300 MHz, ppm in CDCl$_3$)
δ:3.80 (s, 3H), 5.37 (s, 1H), 7.57-7.69 (m, 4H).

Reference Synthetic Examples 17 and 20 to 24

Compounds were synthesized in accordance with Reference Synthetic Example 13.
The morphology and the LC/MS analysis data of the compounds are shown below.

TABLE 2

| Reference Synthetic Examples | Morphology | LC/MS condition | Observed peak (ESI+) | Observed peak (ESI−) | Retention time (min) |
|---|---|---|---|---|---|
| 17 | Yellow orange oil | 2 | 183.00 (M + 1 − Br) | — | 3.30 |
| 20 | Pale yellow oil | 3 | 233 (M + 1 − Br) | — | 3.00 |
| 21 | Red oil | 1 | 179.11 (M + 1 − Br) | — | 3.93 |
| 22 | Pale yellow oil | 3 | 217, 219 (M + 1 − Br) | — | 3.12 |
| 23 | Yellow oil | 3 | 167 (M + 1 − Br) | — | 2.63 |
| 24 | Yellow orange oil | 2 | 167.04 (M + 1 − Br) | — | 3.10 |

Structures of the compounds in Reference Synthetic Examples are shown below.

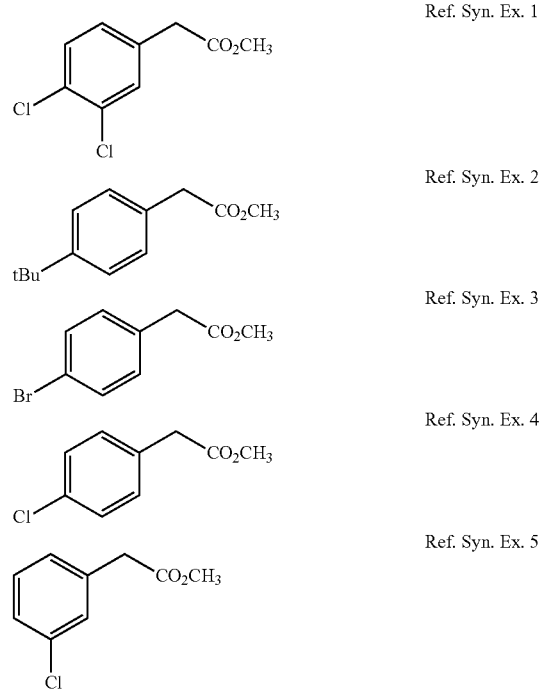

Ref. Syn. Ex. 1

Ref. Syn. Ex. 2

Ref. Syn. Ex. 3

Ref. Syn. Ex. 4

Ref. Syn. Ex. 5

-continued

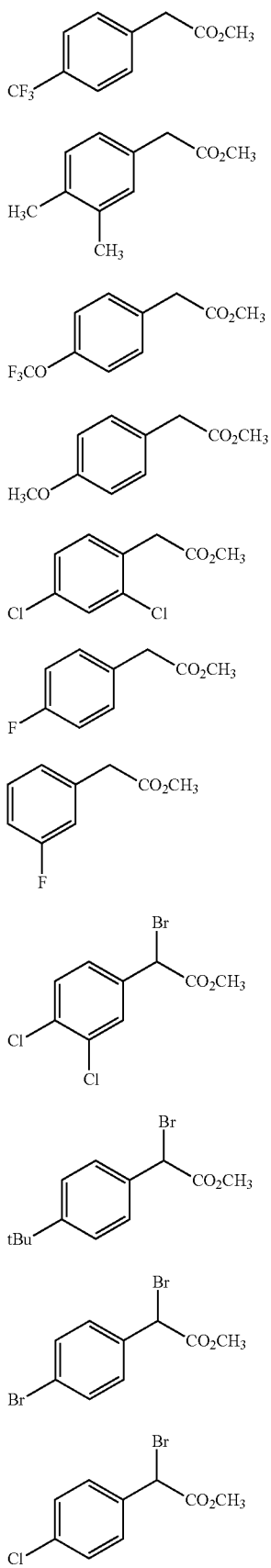

Ref. Syn. Ex. 6

Ref. Syn. Ex. 7

Ref. Syn. Ex. 8

Ref. Syn. Ex. 9

Ref. Syn. Ex. 10

Ref. Syn. Ex. 11

Ref. Syn. Ex. 12

Ref. Syn. Ex. 13

Ref. Syn. Ex. 14

Ref. Syn. Ex. 15

Ref. Syn. Ex. 16

-continued

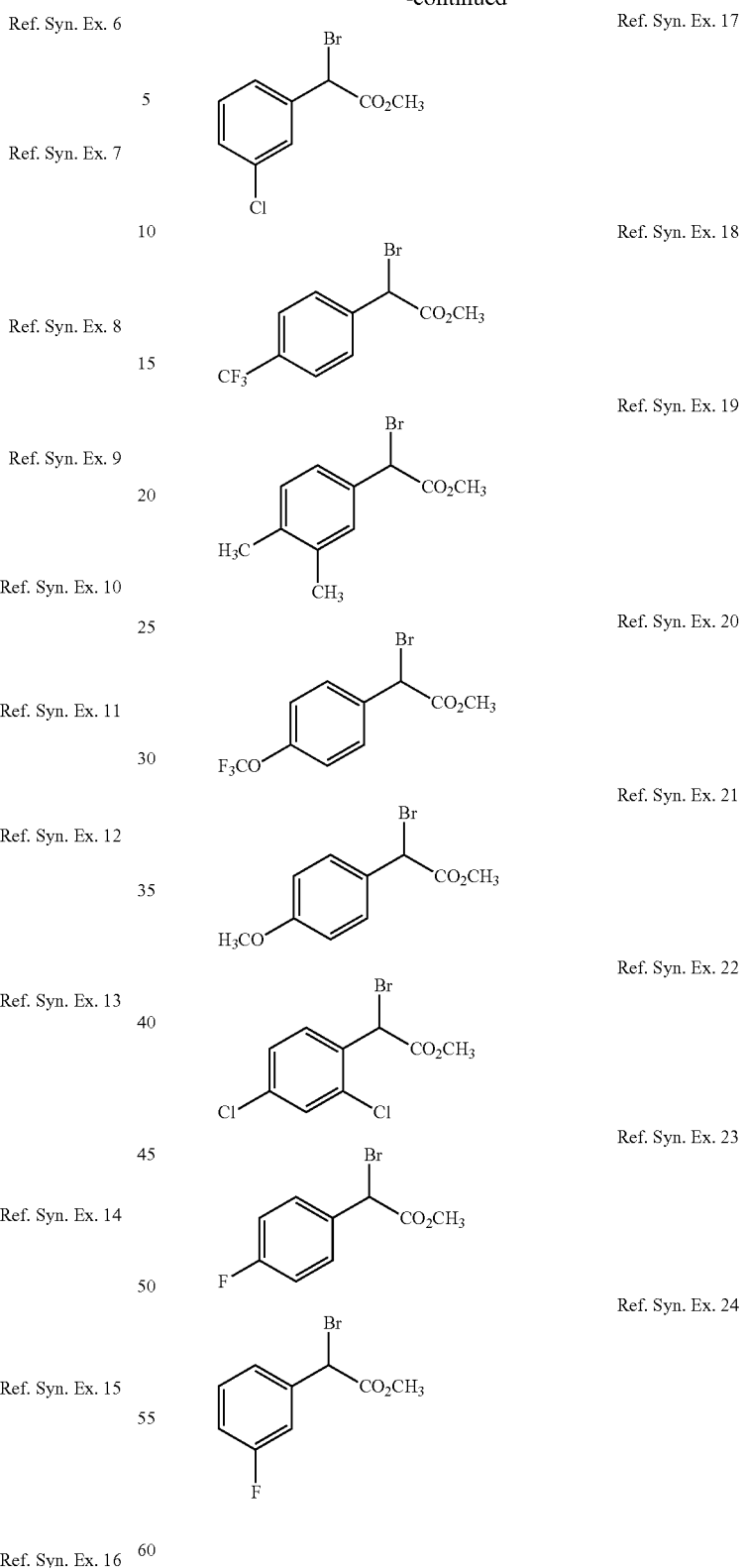

Ref. Syn. Ex. 17

Ref. Syn. Ex. 18

Ref. Syn. Ex. 19

Ref. Syn. Ex. 20

Ref. Syn. Ex. 21

Ref. Syn. Ex. 22

Ref. Syn. Ex. 23

Ref. Syn. Ex. 24

Synthetic Example 1

Methyl 2-thioacetyl-2-(3,4-dichlorophenyl)acetate

A toluene (403 mL) solution of methyl 2-(3,4-dichlorophenyl)-2-bromoacetate (134 g, 0.451 mol) was dropwise added to a methanol (403 mL) solution of potassium thioacetate (67.7 g, 0.586 mol, 1.3 equivalent amounts based on the starting material) at 5° C. over a period of 15 minutes, followed by stirring at 5° C. for 1 hour. The formed solid was subjected to filtration, and the filtrate was mixed with toluene (403 mL), sequentially washed with water, a saturated sodium hydrogencarbonate aqueous solution, a saturated ammonium chloride aqueous solution and a saturated salt solution, and dried over anhydrous magnesium sulfate. The drying agent was removed by filtration, and the solvent was distilled off to give the desired product as a yellow oil (136 g, yield: 103%).

$^1$H NMR (300 MHz, ppm in CDCl$_3$)

δ:2.37 (s, 3H), 3.77 (s, 3H), 5.26 (s, 1H), 7.19-7.26 (m, 1H), 7.39-7.43 (m, 1H), 7.51 (s, 1H).

Synthetic Examples 2, 3 and 6

Compounds were prepared in accordance with Synthetic Example 1.

The NMR analysis data of the compounds are shown below.

Synthetic Example 2

$^1$H-NMR (300 MHz, ppm in CDCl$_3$)

δ 1.31 (s, 9H), 2.36 (s, 3H), 3.74 (s, 3H), 5.30 (s, 1H), 7.28-7.37 (m, 4H).

Synthetic Example 3

$^1$H-NMR (300 MHz, ppm in CDCl$_3$)

δ:2.35 (s, 3H), 3.76 (s, 3H), 5.27 (s, 1H), 7.25-7.29 (m, 2H), 7.45-7.48 (m, 2H).

Synthetic Example 6

$^1$H-NMR (300 MHz, ppm in CDCl$_3$)

δ:2.37 (s, 3H), 3.76 (s, 3H), 5.38 (s, 1H), 7.42-7.62 (m, 4H).

Synthetic Examples 4, 5 and 7 to 12

Compounds were synthesized in accordance with Synthetic Example 1. The morphology and the LC/MS analysis data of the compounds are shown below.

TABLE 3

| Reference Synthetic Examples | Morphology | LC/MS condition | Observed peak (ESI+) | Observed peak (ESI−) | Retention time (min) |
|---|---|---|---|---|---|
| 4 | Red oil | 2 | 259.03 | — | 3.29 |
| 5 | Yellow oil | 1 | 258.90 | 256.95 | 3.92 |
| 7 | Yellow oil | 1 | 252.96 | 250.95 | 4.00 |
| 8 | Colorless oil | 3 | 309 | 307 | 2.97 |
| 9 | Yellow oil | 2 | 276.85 (M + 1 + Na$^+$) | — | 2.45 |
| 10 | Pale yellow oil | 3 | 293, 295 | 291, 293 | 3.00 |
| 11 | Pale yellow oil | 3 | 265 (M + 1 + Na$^+$) | 241 | 2.59 |
| 12 | Yellow oil | 1 | 242.99 | 241.04 | 3.67 |

Synthetic Example 13

Synthesis Method 1

Methyl 2-(3,4-dichlorophenyl)-2-(3-oxobutylthio)acetate

A methanol (400 mL) solution of methyl 2-thioacetyl-2-(3,4-dichlorophenyl)acetate (100 g, 341 mmol) was heated to 60° C., and 35 mass % hydrochloric acid (42.6 mL, 1.5 equivalent amounts) was added, followed by stirring at 60° C. for 4 hours. After the reaction solution was cooled to room temperature, it was dropwise added to an ethyl acetate (400 mL) solution of methyl vinyl ketone (58.3 mL, 1.2 equivalent amounts) and triethylamine (95.1 mL, 2.0 equivalent amounts) at room temperature over a period of 25 minutes, followed by stirring at room temperature for 1 hour. To the reaction solution, ethyl acetate (200 mL) was added, followed by liquid separation with a mixed liquid of water-saturated salt solution (1:1, (v/v)), and the aqueous layer was extracted again with ethyl acetate (100 mL). The extract was combined with the organic layer, washed with a saturated ammonium chloride aqueous solution and a saturated salt solution, and dried over anhydrous magnesium sulfate. The drying agent was removed by filtration, and the solvent was distilled off to give the desired product as an oil (103 g, yield: 94%).

$^1$H-NMR (300 MHz, ppm in CDCl$_3$)

δ:2.20 (s, 3H), 2.70-2.79 (m, 4H), 3.70 (s, 3H), 4.57 (s, 1H), 7.30-7.58 (m, 3H).

Synthesis Method 2

A methanol (280 mL) solution of methyl 2-thioacetyl-2-(3,4-dichlorophenyl)acetate (70 g, 239 mmol) was heated to 60° C., and 35 mass % hydrochloric acid (29.9 mL, 1.5 equivalent amounts) was added, followed by stirring at 60° C. for 3.5 hours. After the reaction solution as cooled to room temperature, it was dropwise added to an ethyl acetate (280 mL) solution of methyl vinyl ketone (24.1 mL, 1.2 equivalent amounts) and triethylamine (66.6 mL, 2.0 equivalent amounts) at room temperature over a period of 30 minutes, followed by stirring at room temperature for 0.5 hour. The reaction solution was mixed with ethyl acetate (140 mL), sequentially washed with a mixed liquid of water-saturated salt solution (1:2, (v/v)), a saturated ammonium chloride aqueous solution and a saturated salt solution, and dried over anhydrous magnesium sulfate. The drying agent was removed by filtration, the solvent was distilled off, and the obtained crude product was mixed with ethyl acetate (140 mL), activated carbon and silica gel and filtered through celite, and the solvent of the filtrate was distilled off to give the desired product as a yellow oil (70.8 g, yield: 92%).

Synthetic Examples 14 and 15

Compounds were prepared in accordance with Synthetic Example 13 (Synthesis Method 2). The NMR analysis data of the compounds are shown below.

Synthetic Example 14

$^1$H-NMR (300 MHz, ppm in CDCl$_3$)

δ:1.30 (s, 9H) 2.11 (s, 3H), 2.64-2.75 (m, 4H), 3.73 (s, 3H), 4.60 (s, 1H), 7.36 (s, 4H).

Synthetic Example 15

$^1$H-NMR (300 MHz, ppm in CDCl$_3$)

δ:2.20 (s, 3H), 2.66-2.76 (m, 4H), 3.69 (s, 3H), 4.57 (s, 1H), 7.33-7.50 (m, 4H).

Synthetic Examples 16 to 24

Compounds were prepared in accordance with Synthetic Example 13 (Synthesis Method 2). The morphology and the LC/MS analysis data of the compounds are shown below.

TABLE 4

| Reference Synthetic Examples | Morphology | LC/MS condition | Observed peak (ESI+) | Observed peak (ESI−) | Retention time (min) |
|---|---|---|---|---|---|
| 16 | Red oil | 1 | 308.79 (M + 1 + Na$^+$) | — | 3.75 |
| 17 | Brown oil | 1 | 286.84 | 285.07 | 3.74 |
| 18 | Brown oil | 4 | 320.85 | — | 3.97 |
| 19 | Reddish brown oil | 1 | 302.88 (M + 1 + Na$^+$) | — | 3.82 |
| 20 | Colorless oil | 3 | 337 | — | 2.85 |
| 21 | Brown oil | 1 | 282.94 | — | 3.35 |
| 22 | Pale yellow oil | 3 | 321, 323 | — | 2.87 |
| 23 | Pale yellow oil | 3 | 293 (M + 1 + Na$^+$) | — | 2.47 |
| 24 | Brown oil | 1 | 292.88 (M + 1 + Na$^+$) | — | 3.52 |

Synthetic Example 25

2-(3,4-Dichlorophenyl)-3-hydroxy-4-methylcarbonyl-2,5-dihyrothiophene

Synthesis Method 1

A methanol (500 mL) solution of sodium amide (19.2 g, purity: 90%, 1.5 equivalent amounts based on the starting material) was heated to 40° C., and to this solution, a methanol (200 mL) solution of methyl 2-(3,4-dichlorophenyl)-2-(3-oxobutylthio)acetate (100 g, purity: 95%, 296 mmol) was dropwise added over a period of 12 minutes, followed by stirring at 40° C. for 1 hour. The reaction solution was cooled to 5° C., water (300 mL) was dropwise added over a period of 10 minutes, and then the solvent was distilled off. To the obtained crude product, chloroform and a saturated ammonium chloride aqueous solution were added, followed by liquid separation, and the organic layer was washed with a saturated salt solution and dried over anhydrous magnesium sulfate. The drying agent was removed by filtration, and the solvent was distilled off to give the desired product as an oil (59.3 g, yield: 65%).

$^1$H-NMR (300 MHz, ppm in CDCl$_3$)
δ:2.17 (s, 3H), 3.79-3.92 (m, 2H), 4.95 (s, 1H), 7.22-7.25 (m, 1H), 7.37-7.43 (m, 1H), 7.50-7.51 (m, 1H).

Synthesis Method 2

A methanol (325 mL) solution of sodium amide (13.2 g, 325 mmol) was heated to 40° C., and to this solution, a methanol (130 mL) solution of methyl 2-(3,4-dichlorophenyl)-2-(3-oxobutylthio)acetate (65 g, 202 mmol) was dropwise added over a period of 20 minutes, followed by stirring at 40° C. for 1 hour. After the reaction mixture was cooled to room temperature, water (13 mL) was dropwise added over a period of 3 minutes, and then the solvent was distilled off. To the obtained crude product, chloroform and a saturated ammonium chloride aqueous solution were added, followed by liquid separation, and the organic layer was washed with a saturated salt solution and dried over anhydrous magnesium sulfate. The drying agent was removed by filtration, and the solvent was distilled off to give the desired product as a brown oil (46.4 g, yield: 79%).

Synthetic Example 26

A compound was prepared in accordance with Synthetic Example 25 (Synthesis Method 2). The product was used for the next step without structural analysis.

Synthetic Examples 27 and 33

Compounds were prepared in accordance with Synthetic Example 25 (Synthesis Method 2). The NMR analysis data of the compounds are shown below.

Synthetic Example 27

$^1$H-NMR (300 MHz, ppm in CDCl$_3$)
δ:2.16 (s, 3H), 3.79-3.91 (m, 2H), 4.97 (s, 1H), 7.25-7.29 (m, 2H), 7.46-7.52 (m, 2H).

Synthetic Example 33

$^1$H-NMR (300 MHz, ppm in CDCl$_3$)
δ:2.14 (s, 3H), 3.80-3.91 (m, 5H), 4.99 (s, 1H), 6.67-6.92 (m, 2H), 7.29-7.34 (m, 2H).

Synthetic Examples 28 to 32 and 34 to 36

Compounds were synthesized in accordance with Synthetic Example 25.

Synthesis Method 2

The morphology and the LC/MS analysis data of the compounds are shown below.

TABLE 5

| Reference Synthetic Examples | Morphology | LC/MS condition | Observed peak (ESI+) | Observed peak (ESI−) | Retention time (min) |
|---|---|---|---|---|---|
| 28 | Red oil | 6 | 254.93 | 252.98 | 2.88 |
| 29 | Red oil | 1 | 254.88 | 252.93 | 4.14 |
| 30 | Brown oil | 4 | 288.90 | 286.96 | 4.39 |
| 31 | Yellowish brown oil | 1 | 248.97 | 247.02 | 4.27 |
| 32 | Brown oil | 3 | 305 | 303 | 3.10 |
| 34 | Brown oil | 3 | 289, 291 | 287, 289 | 3.22 |
| 35 | Brown oil | 3 | 239 | 237 | 2.74 |
| 36 | Red oil | 1 | 238.97 | 237.02 | 3.85 |

Synthetic Example 37

2-(3,4-Dichlorophenyl)-3-hydroxy-4-methylcarbonyl thiophene

A chloroform (967 mL) solution of 2-(3,4-dichlorophenyl)-3-hydroxy-4-methylcarbonyl-2,5-dichlorothiophene (96.7 g, 221 mmol, purity: 63%) was cooled to −18° C., and to this solution, a chloroform (193 mL) solution of sulfuryl chloride (19.5 mL, 1.15 equivalent amounts) was dropwise added over a period of 20 minutes, followed by stirring at −20° C. for 1 hour. The temperature of the solution was raised to 0° C., and water (193 mL) was dropwise added over a period of 5 minutes, followed by liquid separation. The obtained chloroform solution was sequentially washed with water, a saturated salt solution, a saturated sodium hydrogencarbonate aqueous solution, a saturated sodium thiosulfate aqueous solution and a saturated salt solution, and dried over anhydrous magnesium sulfate. The drying agent was removed by filtration, and the solvent was distilled off to obtain a crude product. To the obtained crude product, 2-propanol (967 mL) was added, followed by stirring at 5° C. for 1 hour. The formed crystals were subjected to filtration to give the desired product as a pale yellow solid (49.4 g, yield: 51%).
$^{1}$H-NMR (300 MHz, ppm in CDCl$_{3}$)
δ:2.56 (s, 3H), 7.44 (d, J=8.4 Hz, 1H), 7.62 (dd, J=8.4 Hz, 1.2 Hz, 1H), 7.91-7.93 (m, 2H), 10.51 (s, 1H).

Synthetic Example 38

2-(4-t-Butylphenyl)-3-hydroxy-4-methylcarbonyl thiophene

A chloroform (250 mL) solution of 2-(4-t-butylphenyl)-3-hydroxy-4-methylcarbonyl-2,5-dihydrothiophene (24.94 g, 64.6 mmol, purity: 78%) was cooled to −23° C., and to this solution, a chloroform (50 mL) solution of sulfuryl chloride (5.45 mL, 1.05 equivalent amounts) was dropwise added over a period of 27 minutes, followed by stirring at from −22 to −24° C. for 33 minutes. The temperature of the solution was raised to −3° C., and water (50 mL) was dropwise added over a period of 2.5 minutes, followed by liquid separation. The obtained chloroform solution was sequentially washed with water, a saturated salt solution, a sodium hydroxide aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was distilled in chloroform (80 mL) at 45° C., the solution was cooled to 0° C., and isopropanol (375 mL) was dropwise added, followed by stirring at 0° C. for 40 minutes. The formed crystals were subjected to filtration to give the desired product as a yellow solid (15.5 g, yield: 63%).
LC/MS: Condition 2, Retention time 4.54 (min)
LC/MS (ESI$^{+}$) m/z; 297, 299 [M+1]
LC/MS (ESI$^{-}$) m/z; 295, 297 [M−1]

Synthetic Example 39

2-(4-Bromophenyl)-3-hydroxy-4-methylcarbonyl thiophene

A chloroform (249 mL) solution of 2-(4-bromophenyl)-3-hydroxy-4-methylcarbonyl-2,5-dihydrothiophene (24.9 g, 64.6 mmol, purity: 78%) was cooled to −23° C., and a chloroform (50 mL) solution of sulfuryl chloride (5.45 mL, 1.05 equivalent amounts) was dropwise added over a period of 27 minutes, followed by stirring at −20° C. for 1 hour. The temperature of the solution was raised to −5° C., and water (50 mL) was dropwise added over a period of 3 minutes, followed by liquid separation. The obtained chloroform solution was sequentially washed with water, a saturated salt solution, a sodium hydroxide aqueous solution, a saturated sodium thiosulfate aqueous solution and a saturated salt solution, and dried over anhydrous magnesium sulfate. The drying agent was removed by filtration, and the solvent was distilled off to obtain a crude product. To the obtained crude product, 2-propanol (374 mL) was added, followed by stirring at 0° C. for 40 minutes. The formed crystals were removed by filtration to give the desired product as a yellow solid (15.7 g, yield: 63%).
LC/MS: Condition 1, Retention time 4.54 (min)
LC/MS (ESI$^{+}$) m/z: 297, 299 [M+1]

Synthetic Example 40

2-(4-Chlorophenyl)-3-hydroxy-4-methylcarbonyl thiophene

A chloroform (100 mL) solution of 2-(4-chlorophenyl)-3-hydroxy-4-methylcarbonyl-2,5-dihydrothiophene (10.00 g, 37.29 mmol, purity: 95%) was cooled to −40° C., and to this solution, a chloroform (150 mL) solution of sulfuryl chloride (3.6 mL, 1.2 equivalent amounts) was dropwise added over a period of 50 minutes, followed by stirring at −35° C. for 40 minutes. The temperature of the solution was raised to −3° C., and water (20 mL) was dropwise added, followed by liquid separation. The obtained chloroform solution was sequentially washed with water, a saturated salt solution, a saturated sodium hydrogencarbonate aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was suspended in isopropyl alcohol (100 mL) at room temperature, followed by stirring at 0° C. for 15 minutes. The formed crystals were subjected to filtration to give the desired product as a yellow solid (7.26 g, yield: 77%).
LC/MS: Condition 6, Retention time 3.17 (min)
LC/MS (ESI$^{+}$) m/z; 252.92, 254.87 [M+1]
LC/MS (ESI$^{-}$) m/z; 250.97, 252.92 [M−1]

Synthetic Example 41

2-(3-Chlorophenyl)-3-hydroxy-4-methylcarbonyl thiophene

A chloroform (25 mL) solution of 2-(3-chlorophenyl)-3-hydroxy-4-methylcarbonyl-2,5-dihydrothiophene (2.49 g, 8.02 mmol, purity: 82%) was cooled to −43° C., and to this solution, a chloroform (50 mL) solution of sulfuryl chloride (0.77 mL, 1.1 equivalent amounts) was dropwise added over a period of 32 minutes, followed by stirring at −15° C. for 1 hour. The temperature of the solution was raised to 0° C., and water (5 mL) was dropwise added, followed by liquid separation. The obtained chloroform solution was sequentially washed with water, a saturated salt solution, a sodium hydroxide aqueous solution, a saturated sodium thiosulfate aqueous solution and a saturated salt solution, and dried over anhydrous magnesium sulfate. The drying agent was removed by filtration, and the solvent was distilled off to give the desired product as a yellow solid (2.0 g, yield: 99%).
LC/MS: Condition 1, Retention time 4.49 (min)
LC/MS (ESI$^{+}$) m/z; 252.87 254.82 [M+1]
LC/MS (ESI$^{-}$) m/z; 250.92 252.93 [M−1]

Synthetic Example 42

2-(4-Trifluoromethylphenyl)-3-hydroxy-4-methylcarbonyl thiophene

A chloroform (223 mL) solution of 2-(4-trifluoromethylphenyl)-3-hydroxy-4-methylcarbonyl-2,5-dihydrothiophene (22.25 g, 69.46 mmol, purity: 90%) was cooled to −46° C., and to this solution, a chloroform (334 mL) solution of sulfuryl chloride (6.70 mL, 1.2 equivalent amounts) was dropwise added over a period of 10 minutes, followed by stirring at −4° C. for 10 minutes. The temperature of the solution was raised to 0° C., and water (45 mL) was dropwise added thereto over a period of 15 minutes, followed by liquid separation. The obtained chloroform solution was sequentially washed with water, a saturated salt solution, a saturated sodium hydrogencarbonate aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was isolated and purified by silica gel column chromatography (eluent: hexane/chloroform=1/1 (v/v)) to give the desired product as a yellow solid (14.78 g, yield: 69%).

LC/MS: Condition 2, Retention time 3.70 (min)
LC/MS (ESI$^+$) m/z; 286.90 [M+1]
LC/MS (ESI$^-$) m/z; 284.95 [M−1]

Synthetic Example 43

2-(3,4-Dimethylphenyl)-3-hydroxy-4-methylcarbonyl thiophene

A chloroform (24 mL) solution of 2-(3,4-dimethylphenyl)-3-hydroxy-4-methylcarbonyl-2,5-dihydrothiophene (2.44 g, 9.82 mmol, purity: 72%) was cooled to −40° C., and to this solution, a chloroform (37 mL) solution of sulfuryl chloride (0.79 mL, 1.0 equivalent amount) was dropwise added over a period of 55 minutes, followed by stirring at −40° C. for 60 minutes. The temperature of the solution was raised to 0° C., and water (5 mL) was dropwise added over a period of 1 minute, followed by liquid separation. The obtained chloroform solution was sequentially washed with water, a saturated salt solution, a saturated sodium hydrogencarbonate aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was suspended in isopropyl alcohol (37 mL) at room temperature, followed by stirring at 0° C. for 30 minutes. The formed crystals were subjected to filtration to give the desired product (0.47 g, yield: 20%) as a yellow solid. Further, the filtrate was isolated and purified by silica gel column chromatography (eluent: hexane/ethyl acetate=3/1 (v/v)) to give the desired product (0.81 g, yield: 33%) as a yellow solid (1.28 g, yield: 53%).

LC/MS: Condition 1, Retention time 4.52 (min)
LC/MS (ESI$^+$) m/z; 246.95 [M+1]
LC/MS (ESI$^+$) m/z; 245.00 [M−1]

Synthetic Example 44

2-(4-Trifluoromethoxyphenyl)-3-hydroxy-4-methylcarbonyl thiophene

A chloroform (45 mL) solution of 2-(4-trifluoromethoxyphenyl)-3-hydroxy-4-methylcarbonyl-2,5-dihydrothiophene (4.5 g, 12.6 mmol, purity: 85%) was cooled to −5° C., and to this solution, a chloroform (90 mL) solution of sulfuryl chloride (1.1 mL, 1.1 equivalent amounts) was dropwise added over a period of 30 minutes, followed by stirring at −15° C. for 1 hour. The temperature of the solution was raised to 0° C., and water (11 mL) was dropwise added, followed by liquid separation. The obtained chloroform solution was sequentially washed with water, a saturated salt solution, a sodium hydroxide aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was purified by silica gel column chromatography (eluent: hexane/ethyl acetate) to give the desired product as a yellow solid (3.15 g, yield: 83%).

LC/MS: Condition 3, Retention time 3.34 (min)
LC/MS (ESI$^+$) m/z; 303 [M+1]
LC/MS (ESI$^+$) m/z; 301 [M−1]

Synthetic Example 45

2-(4-Methoxyphenyl)-3-hydroxy-4-methylcarbonyl thiophene

A chloroform (67 mL) solution of 2-(4-methoxyphenyl)-3-hydroxy-4-methylcarbonyl-2,5-dihydrothiophene (6.67 g, 18.45 mmol, purity: 80%) was cooled to −16° C., and to this solution, a chloroform (13 mL) solution of sulfuryl chloride (1.78 mL, 1.2 equivalent amounts) was dropwise added over a period of 20 minutes, followed by stirring at −12° C. for 42 minutes. The temperature of the solution was raised to −3° C., and water (13 mL) was dropwise added over a period of 5 minutes, followed by liquid separation. The obtained chloroform solution was sequentially washed with water, a saturated salt solution, a saturated sodium hydrogencarbonate aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was isolated and purified by silica gel column chromatography (eluent: hexane/ethyl acetate/chloroform=7.5/2.5/1 (v/v/v)) to give the desired product as a yellow solid (4.83 g, yield: 73%).

$^1$H-NMR (300 MHz, ppm in CDCl$_3$)
δ:2.56 (s, 3H), 3.83 (s, 3H), 4.99 (s, 1H), 6.92-6.95 (m, 2H), 7.69-7.72 (m, 2H), 7.83 (s, 1H), 10.23 (s, 1H).

Synthetic Example 46

2-(2,4-Dichlorophenyl)-3-hydroxy-4-methylcarbonyl thiophene

A chloroform (3 mL) solution of 2-(2,4-dichlorophenyl)-3-hydroxy-4-methylcarbonyl-2,5-dihydrothiophene (0.3 g, 0.93 mmol, purity: 90%) was cooled to −36° C., and to this solution, a chloroform (5 mL) solution of sulfuryl chloride (0.082 mL, 1.2 equivalent amounts) was dropwise added over a period of 10 minutes, followed by stirring at −25° C. for 40 minutes. The temperature of the solution was raised to 5° C., and water (0.6 mL) was dropwise added, followed by liquid separation. The obtained chloroform solution was sequentially washed with water, a saturated salt solution, a sodium hydroxide aqueous solution, a saturated sodium thiosulfate aqueous solution and a saturated salt solution, and dried over anhydrous magnesium sulfate. The drying agent was removed by filtration, and the solvent was distilled off to give the desired product as a yellow solid (0.27 g, yield: 91%).

LC/MS: Condition 3, Retention time 3.29 (min)
LC/MS (ESI$^+$) m/z; 287, 289, 291 [M+1]
LC/MS (ESI$^+$) m/z; 285, 287, 289 [M−1]

Synthetic Example 47

2-(4-Fluorophenyl)-3-hydroxy-4-methylcarbonyl thiophene

A chloroform (6.3 mL) solution of 2-(4-fluorophenyl)-3-hydroxy-4-methylcarbonyl-2,5-dihydrothiophene (0.63 g, 2.38 mmol, purity: 90%) was cooled to −12° C., and to this solution, a chloroform (1.3 mL) solution of sulfuryl chloride (0.23 mL, 1.2 equivalent amounts) was dropwise added over a period of 6 minutes, followed by stirring at −11° C. for 2 hours. The temperature of the solution was raised to 3° C., and water (1.3 mL) was dropwise added, followed by liquid separation. The obtained chloroform solution was sequentially washed with water, a saturated salt solution, a sodium hydroxide aqueous solution, a saturated sodium thiosulfate aqueous solution and a saturated salt solution, and dried over anhydrous magnesium sulfate. The drying agent was removed by filtration, and the solvent was distilled off to give the desired product as a yellow solid (0.28 g, yield: 50%).

LC/MS: Condition 3, Retention time 2.99 (min)
LC/MS (ESI$^+$) m/z; 237 [M+1]
LC/MS (ESI$^+$) m/z; 235 [M−1]

Synthetic Example 48

2-(3-Fluorophenyl)-3-hydroxy-4-methylcarbonyl thiophene

A chloroform (6.2 mL) solution of 2-(3-fluorophenyl)-3-hydroxy-4-methylcarbonyl-2,5-dihydrothiophene (0.61 g, 2.58 mmol, purity: 78%) was cooled to −40° C., and to this solution, a chloroform (1.2 mL) solution of sulfuryl chloride (0.21 mL, 1.0 equivalent amount) was dropwise added over a period of 3 minutes. The temperature of the solution was raised to 0° C., and water (1.2 mL) was dropwise added over a period of 1 minute, followed by liquid separation. The obtained chloroform solution was sequentially washed with water, a saturated salt solution, a saturated sodium hydrogencarbonate aqueous solution, a saturated sodium thiosulfate aqueous solution and a saturated salt solution, and dried over anhydrous magnesium sulfate. The drying agent was removed by filtration, and the solvent was distilled off to obtain a crude product. The obtained crude product was isolated and purified by column chromatography (eluent: hexane/ethyl acetate=5/1 (v/v)) to give the desired product as a green solid (0.27 g, yield: 44%).

LC/MS: Condition 1, Retention time 4.22 (min)
LC/MS (ESI$^+$) m/z; 236.956 [M+1]
LC/MS (ESI$^+$) m/z; 235.00 [M−1]

Synthetic Example 49

Methyl 2-(3,4-dichlorophenyl)-2-(3-oxo-1-methylbutylthio)acetate

A methanol (6.8 mL) solution of methyl 2-thioacetyl-2-(3,4-dichlorophenyl)acetate (1.0 g, 3.4 mmol) synthesized in Synthetic Example 1 was heated to 60° C., and to this solution, 35 mass % hydrochloric acid (0.43 mL) was added, followed by stirring at from 52 to 56° C. for 4 hours. After the reaction solution was cooled to room temperature, it was dropwise added to a N,N-dimethylformamide (6.8 mL) solution of 3-buten-2-one (0.67 mL, 2 equivalent amounts) and triethylamine (0.95 mL, 2.0 equivalent amounts) at room temperature over a period of 8 minutes, followed by stirring at room temperature for 2 hours. The reaction solution was mixed with ethyl acetate (50 mL), sequentially washed with a mixed liquid of water-saturated salt solution (1:1, (v/v)), a saturated ammonium chloride aqueous solution and a saturated salt solution, and dried over anhydrous magnesium sulfate. The drying agent was removed by filtration, and the solvent was distilled off to give the desired product as a pale yellow oil (1.08 g, yield: 95%).

Synthetic Example 50

2-(3,4-Dichlorophenyl)-3-hydroxy-4-methylarbonyl-5-methyl-2,5-dihydrothiophene

A 2-propanol (8 mL) solution of methyl 2-(3,4-dichlorophenyl)-2-(3-oxo-1-methylbutylthio)acetate (1.07 g, 3.20 mmol) and sodium amide (0.17 g, purity: 90%, 1.2 equivalent amounts based on the starting material) was stirred at room temperature for 1.5 hours. The reaction solution was mixed with a saturated ammonium chloride aqueous solution (15 mL) and then with water, and the solvent was distilled off. The obtained crude product containing water was extracted with ethyl acetate, and the extract was dried over a drying agent. The drying agent was removed by filtration, and the solvent was distilled off to give the desired product as a red oil (0.92 g, yield: 95%).

Synthetic Example 51

2-(3,4-Dichlorophenyl)-3-hydroxy-4-methylcarbonyl-5-methylthiophene

A dichloromethane (13 mL) solution of 2-(3,4-dichlorophenyl)-3-hydroxy-4-methylcarbonyl-5-methyl-2,5-dihydrothiophene (806 mg, 2.66 mmol) was cooled to −72° C., and to this solution, a dichloromethane (2.7 mL) solution of sulfuryl chloride (0.11 mL, 0.5 equivalent amount) was dropwise added over a period of 3 minutes. After the temperature of the solution was raised to room temperature, the solution was mixed with water (16 mL) and a saturated sodium chloride aqueous solution (16 mL), and extracted with dichloromethane. The dichloromethane solution was dried over a drying agent and purified by silica gel column chromatography (eluent: hexane/ethyl acetate=85/15 and then 4/1 (v/v)) to give the desired product as a yellow solid (0.25 g, yield: 31%).

Synthetic Example 52

The same reaction as in Synthetic Example 1 was carried out using the same materials under the same reaction conditions except that the equivalent amount of potassium thioacetate was changed to 1.6 equivalent amounts based on the starting material. The yield was 91%.

Synthetic Example 53

The same reaction as in Synthetic Example 1 was carried out using the same materials under the same reaction conditions except that the reaction temperature was changed to 29° C. The yield was 92%.

Synthetic Example 54

Methyl 2-(3,4-dichlorophenyl)-2-(3-oxobutylthio)acetate

To a methanol (2 mL) solution of methyl 2-thioacetyl-2-(3,4-dichlorophenyl)acetate (0.50 g, 1.7 mmol), concentrated sulfuric acid (0.050 mL, 0.55 equivalent amount) was added, followed by stirring at 60° C. for 3 hours. After the reaction solution was cooled to room temperature, it was dropwise added to an ethyl acetate (2 mL) solution of methyl vinyl ketone (0.17 mL, 1.2 equivalent amounts) and triethylamine (0.36 mL, 1.5 equivalent amount) at room temperature. The reaction solution was mixed with ethyl acetate (1 mL), followed by liquid separation with a mixed liquid of water-saturated salt solution (1:1, (v/v)), and further, the organic layer was washed with a saturated ammonium chloride aqueous solution and a saturated salt solution and dried over anhydrous magnesium sulfate. The drying agent was removed by filtration, and the solvent was distilled off to give the desired product as a colorless oil (0.42 g, yield: 76%).

Synthetic Example 55

Methyl 2-thioacetyl-2-(4-t-butylphenyl)acetate

To a methanol (203 g) solution of potassium thioacetate (70.4 g, 0.616 mol, 1.3 equivalent amounts based on the starting material), a mixed solution of a 33 mass % methanol solution (408.5 g, 0.473 mol) of methyl 2-(4-t-butylphenyl)-2-bromoacetate and methanol (270 g) was dropwise added over a period of 1 hour and 20 minutes, followed by stirring at from 30 to 40° C. for 1 hour. Then, the reaction solution was mixed with heptane (674 g) and water (675 g) and stirred for 20 minutes, followed by liquid separation. The solvent was distilled off from the obtained organic layer under reduced pressure at 40° C. until the total amount became 382 g. The obtained solution was cooled to 30° C. over a period of 1 hour, and 0.13 g of seed crystals were added. Then, the solution was stirred for 1 hour and further cooled to −10° C. over a period of 3 hours. Then, the solution was stirred for 1 hour and subjected to filtration, and the obtained crystals were dried to give the desired product (110.7 g, yield: 83.3%).

Synthetic Example 56

Methyl 2-(4-t-butylphenyl)-2-(3-oxobutylthio)acetate

To a methanol (200 g) solution of methyl 2-thioacetyl-2-(4-t-butylphenyl)acetate (100 g, 0.357 mol), 35 mass hydrochloric acid (9.29 g, 0.25 equivalent amount) was added, and the solution was heated to 63° C. and stirred for 5 hours and 27 minutes. Then, the reaction liquid was cooled to the vicinity of 30° C. The obtained solution was dropwise added to a mixed solution of toluene (400 g), triethylamine (27.1 g, 0.75 equivalent amount) and methyl vinyl ketone (30.3 g, 1.2 equivalent amounts) at from 25 to 26° C. over a period of 1 hour and 37 minutes, followed by stirring at 25° C. for 1 hour and 43 minutes. To the reaction solution, 35 mass % hydrochloric acid (22.3 g, 0.60 equivalent amount), toluene (500 g) and water (502 g) were added, followed by liquid separation, and the obtained organic layer was washed with water (500 g). Then, the solvent of the organic layer was distilled off under reduced pressure, and toluene (378 g) was added to give a 16.7 mass % toluene solution of the desired product (618 g, quantitative yield by HPLC: 93.9%).

Synthetic Example 57

2-(4-t-Butylphenyl)-3-hydroxy-4-methylcarbonyl-2,5-dihydrothiophene

Methyl 2-(4-t-butylphenyl)-2-(3-oxobutylthio)acetate (540 g, 16.7 mass % toluene solution) was dropwise added to a solution of a 28 mass % methanol solution of sodium methoxide (112.6 g, 2.0 equivalent amounts based on the starting material), toluene (451 g) and isopropanol (90 g) at from 20 to 30° C. over a period of 31 minutes, followed by stirring at from 20 to 30° C. for 2 hours. This solution was dropwise added to a mixed solution of 35 mass % hydrochloric acid (63.8 g, 2.1 equivalent amounts), water (386 g) and toluene (180 g) at from 20 to 30° C. over a period of 1 hour. After stirring for 1 hour, liquid separation was carried out, and the obtained organic layer was washed with water (450 g). Then, the solvent of the organic layer was distilled off under reduced pressure to give the desired product as a 11.2 mass % methanol solution (665 g, quantitative yield by HPLC: 92.6%).

Synthetic Example 58

2-(4-t-Butylphenyl)-3-hydroxy-4-methylcarbonylthiophen

A solution having methanol (121.20 g) added to a 11.2 mass % methanol solution (539.0 g, 217.08 mmol) of 2-(4-t-butylphenyl)-3-hydroxy-4-methylcarbonyl-2,5-dihydrothiophene was heated to 51° C., and a 30 mass % hydrogen peroxide solution (61.6 g, 2.5 equivalent amounts) was dropwise added over a period of 30 minutes, followed by stirring at from 50 to 52° C. for 5 hours. Then, the solution was cooled to 25 to 30° C., and then toluene, heptane and water were added, followed by liquid separation. Then, to the obtained organic layer, a 7 mass % sodium hydrogencarbonate aqueous solution, toluene and heptane were added, followed by liquid separation, and further, the obtained organic layer was washed with a 3 mass % salt solution. The solvent was distilled off under reduced pressure from the obtained organic layer to give a 26.6 mass % solution of the desired product. To the obtained solution, methanol was added to adjust the concentration to 9 mass %, and the solution was heated to from 55 to 60° C. to dissolve the formed solid. To this solution, 24.2 g of water was further dropwise added, followed by stirring for 1 hour. Then, the solution was cooled to −10° C. and stirred for 1 hour. The formed crystals were subjected filtration to give the desired product as yellow crystals (44.2 g, yield: 73.9%).

Structures of the compounds in Synthetic Examples 1 to 51 are shown below.

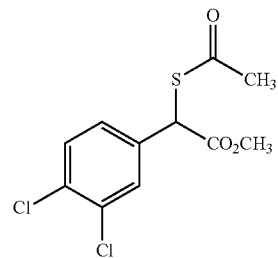

Synthetic Example 1

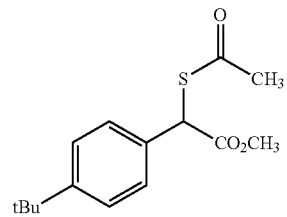

Synthetic Example 2

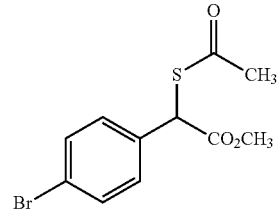

Synthetic Example 3

Synthetic Example 4
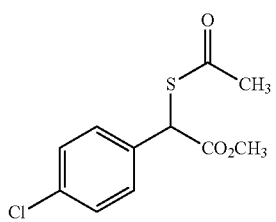
Synthetic Example 5
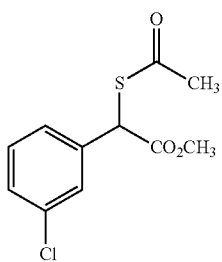
Synthetic Example 6
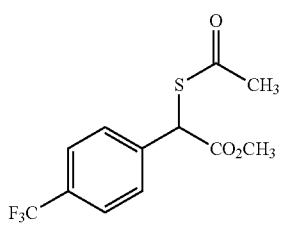
Synthetic Example 7
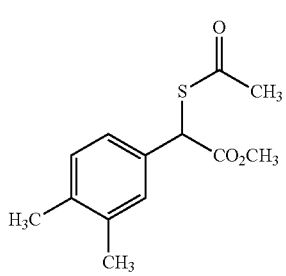
Synthetic Example 8
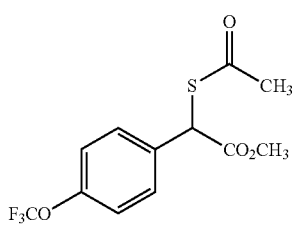
Synthetic Example 9
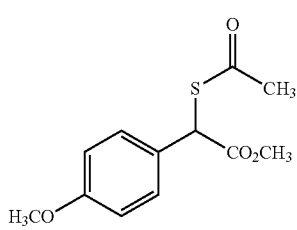
Synthetic Example 10
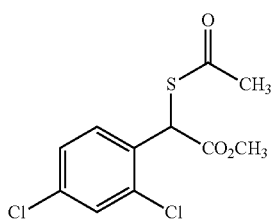
Synthetic Example 11
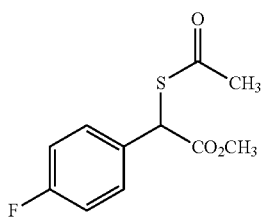
Synthetic Example 12
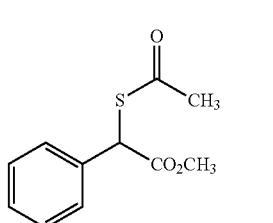
Synthetic Example 13
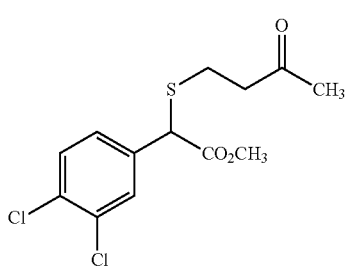
Synthetic Example 14
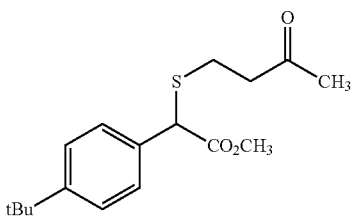
Synthetic Example 15
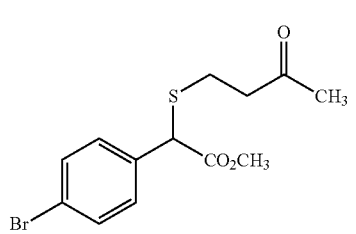

Synthetic Example 16
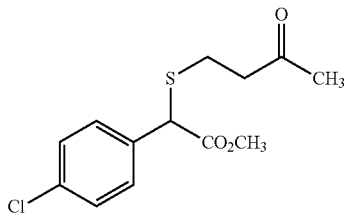
Synthetic Example 17
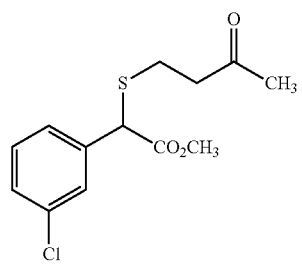
Synthetic Example 18
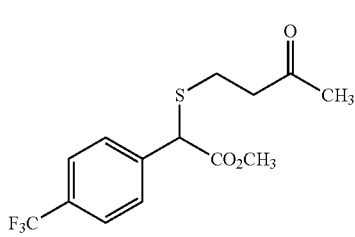
Synthetic Example 19
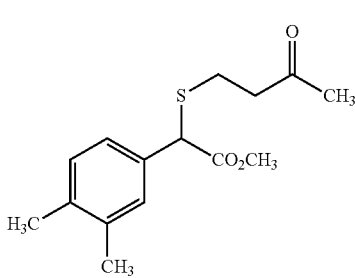
Synthetic Example 20
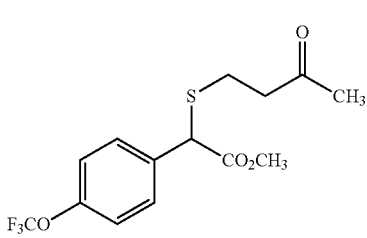
Synthetic Example 21
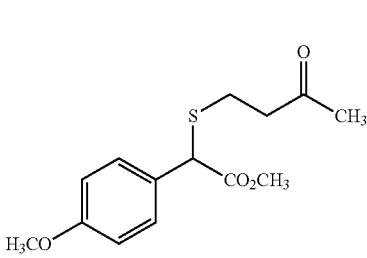
Synthetic Example 22
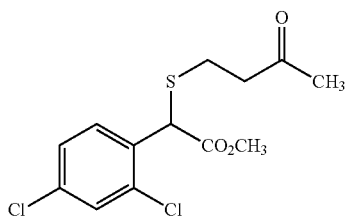
Synthetic Example 23
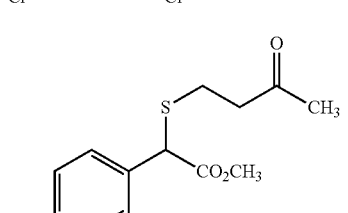
Synthetic Example 24
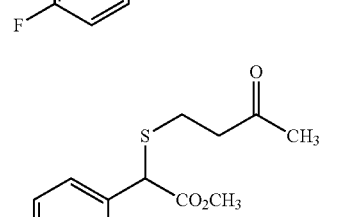
Synthetic Example 25
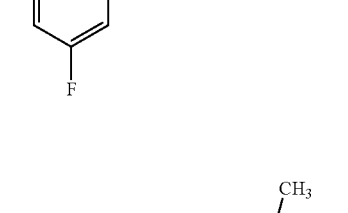
Synthetic Example 26
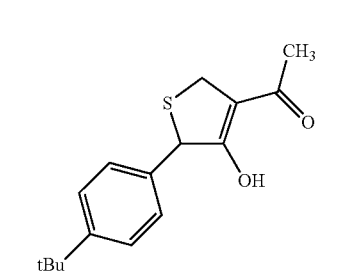
Synthetic Example 27
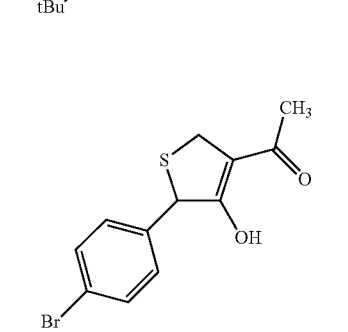

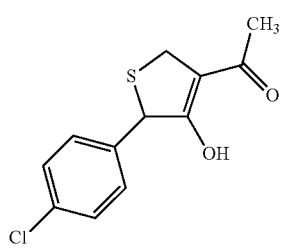
Synthetic Example 28
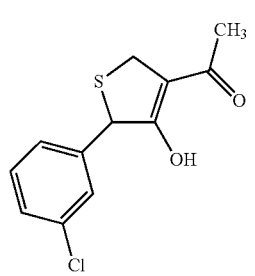
Synthetic Example 29
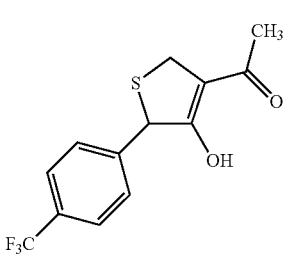
Synthetic Example 30
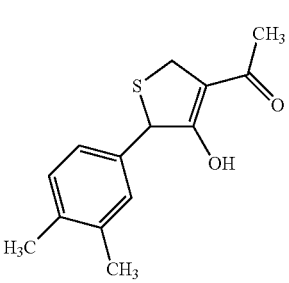
Synthetic Example 31
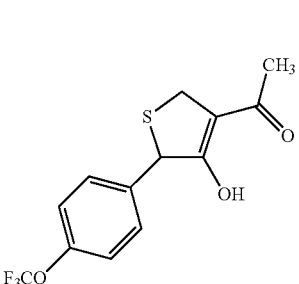
Synthetic Example 32
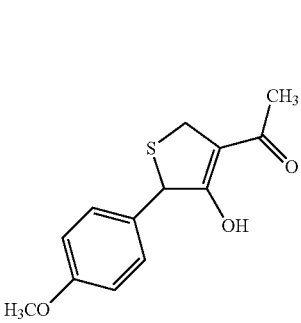
Synthetic Example 33
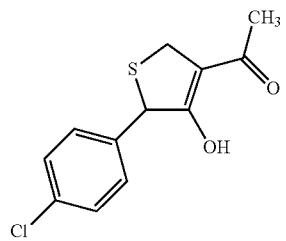
Synthetic Example 34
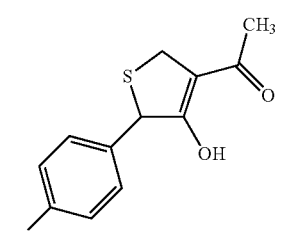
Synthetic Example 35
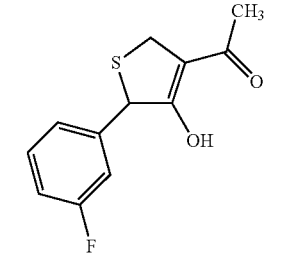
Synthetic Example 36
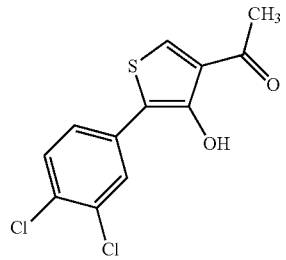
Synthetic Example 37
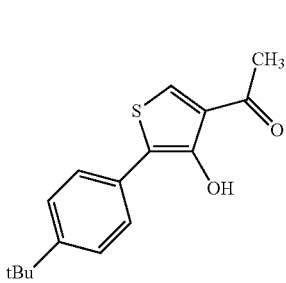
Synthetic Example 38
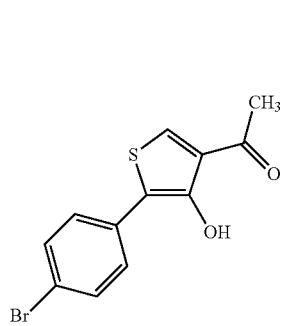
Synthetic Example 39

Synthetic Example 40
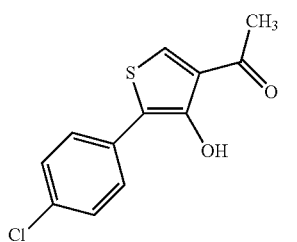
Synthetic Example 41
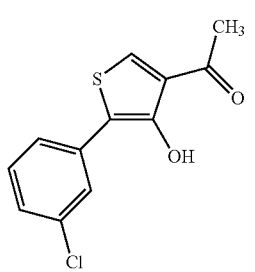
Synthetic Example 42
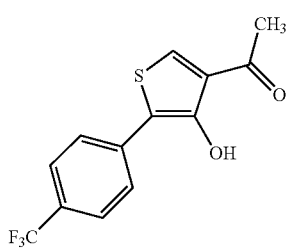
Synthetic Example 43
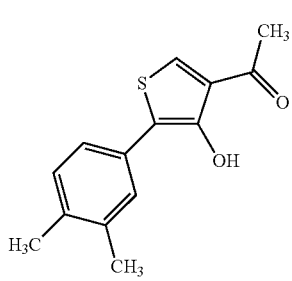
Synthetic Example 44
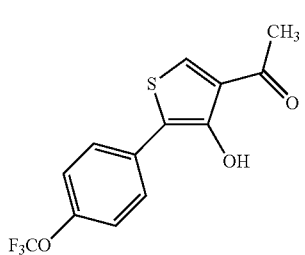
Synthetic Example 45
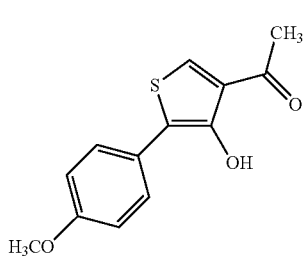
Synthetic Example 46
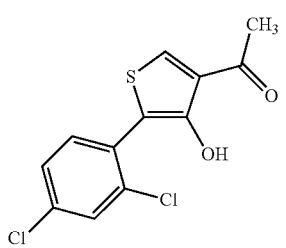
Synthetic Example 47
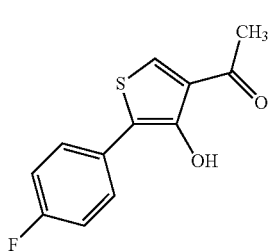
Synthetic Example 48
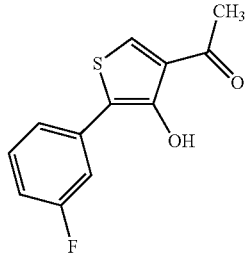
Synthetic Example 49
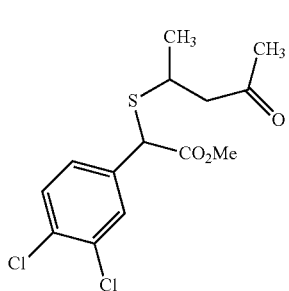
Synthetic Example 50
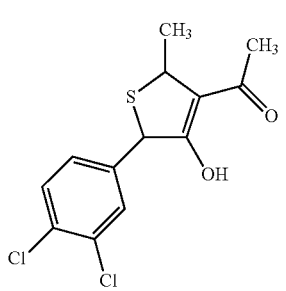
Synthetic Example 51
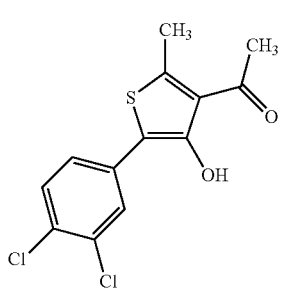

INDUSTRIAL APPLICABILITY

The 2-aryl-3-hydroxy-4-substituted carbonyl thiophene compounds obtained by the production process of the present invention are industrially useful compounds as intermediates for production of medicines and agricultural chemicals, for example, as intermediates for synthesis of thrombopoietin receptor activators (e.g. WO2004/10868).

The entire disclosure of Japanese Patent Application No. 2008-049371 filed on Feb. 29, 2008 including specification, claims and summary is incorporated herein by reference in its entirety.

The invention claimed is:

1. A dihydrothiophene compound represented by the formula (6):

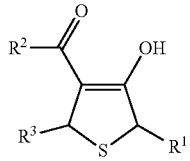

(6)

wherein:
R$^1$ represents a C$_{6-10}$ aryl group or a C$_{1-5}$ heteroaryl group, unsubstituted or substituted with one or more halogen atoms, one or more carboxy groups, one or more nitro groups, one or more formyl groups, one or more cyano groups, one or more hydroxy groups, one or more protected hydroxy groups, one or more thiol groups, one or more amino groups, one or more C$_{1-10}$ alkyl groups, one or more C$_{2-6}$ alkenyl groups, one or more C$_{2-6}$ alkynyl groups, one or more C$_{1-10}$ alkoxy groups, one or more C$_{1-10}$ alkylcarbonyl groups, one or more C$_{1-10}$ alkylcarbonyloxy groups, one or more C$_{1-10}$ alkoxycarbonyl groups or one or more C$_{6-10}$ aryl groups, such that the C$_{1-10}$ alkyl groups, the C$_{2-6}$ alkenyl groups, the C$_{2-6}$ alkynyl groups, the C$_{1-10}$ alkoxy groups, the C$_{1-10}$ alkylcarbonyl groups, the C$_{1-10}$ alkylcarbonyloxy groups, the C$_{1-10}$ alkoxycarbonyl groups and the C$_{6-10}$ aryl groups are unsubstituted or substituted with one or more halogen atoms;

R$^2$ and R$^3$ independent represent a hydrogen atom, a C$_{1-6}$ alkyl group or a C$_{6-10}$ aryl group, unsubstituted or substituted with one or more halogen atoms, one or more nitro groups, one or more cyano groups, one or more hydroxy groups, one or more protected hydroxy groups, one or more thiol groups, one or more amino groups, one or more C$_{1-10}$ alkyl groups, one or more C$_{2-6}$ alkenyl groups, one or more C$_{2-6}$ alkynyl groups, one or more C$_{1-10}$ alkoxy groups or one or more C$_{6-10}$ aryl groups, such that the C$_{1-10}$ alkyl groups, the C$_{2-6}$ alkenyl groups, the C$_{2-6}$ alkynyl groups, the C$_{1-10}$ alkoxy groups and the C$_{6-10}$ aryl groups are unsubstituted or substituted with one or more halogen atoms.

2. The dihydrothiophene compound according to claim 1, wherein:
R$^1$ is a C$_{6-10}$ aryl group unsubstituted or substituted with one or more halogen atoms, one or more C$_{1-10}$ alkyl groups or one or more C$_{1-10}$ alkoxy groups, such that the C$_{1-10}$ alkyl groups and the C$_{1-10}$ alkoxy groups are unsubstituted or substituted with one or more halogen atoms;

R$^2$ is a C$_{1-3}$ alkyl group unsubstituted or substituted with one or more halogen atoms; and R$^3$ is a hydrogen atom or a methyl group.

3. The dihydrothiophene compound according to claim 2, wherein R$^1$ is a phenyl group unsubstituted or substituted with one or more halogen atoms, one or more C$_{1-10}$ alkyl groups or one or more C$_{1-10}$ alkoxy groups, such that the C$_{1-10}$ alkyl groups and the C$_{1-10}$ alkoxy groups are unsubstituted or substituted with one or more halogen atom.

4. A dihydrothiophene compound represented by any one of the following formulae:

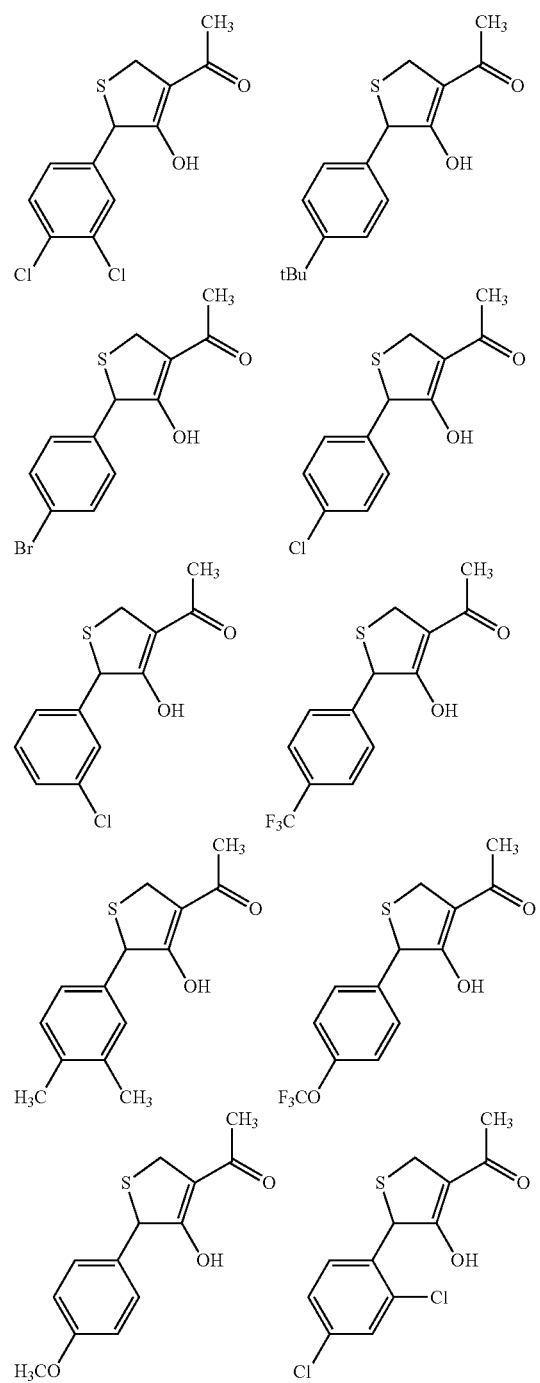

-continued
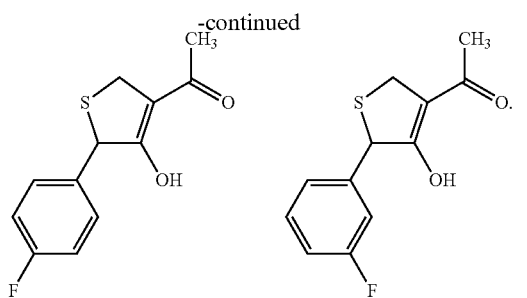
* * * * *